(12) United States Patent
Yodfat et al.

(10) Patent No.: US 8,454,510 B2
(45) Date of Patent: Jun. 4, 2013

(54) METHOD AND DEVICE FOR ASSESSING CARBOHYDRATE-TO-INSULIN RATIO

(75) Inventors: Ofer Yodfat, Maccabim-Reut (IL); Gali Shapira, Haifa (IL); Iddo Gescheit, Tel-Aviv (IL)

(73) Assignee: Medingo Ltd., Yoqneam Illit (IL)

( * ) Notice: Subject to any disclaimer, the term of this patent is extended or adjusted under 35 U.S.C. 154(b) by 1180 days.

(21) Appl. No.: 12/143,601

(22) Filed: Jun. 20, 2008

(65) Prior Publication Data

US 2009/0018406 A1    Jan. 15, 2009

Related U.S. Application Data

(60) Provisional application No. 60/936,690, filed on Jun. 20, 2007.

(51) Int. Cl.
*A61B 5/00* (2006.01)

(52) U.S. Cl.
USPC .......................................... 600/365; 600/301

(58) Field of Classification Search
USPC .................................................. 600/301, 365
See application file for complete search history.

(56) References Cited

U.S. PATENT DOCUMENTS

| | | | |
|---|---|---|---|
| 6,936,029 | B2 | 8/2005 | Mann |
| 2003/0055570 | A1 | 3/2003 | Ribeiro, Jr. |
| 2005/0049179 | A1 | 3/2005 | Davidson et al. |
| 2007/0191702 | A1 | 8/2007 | Yodfat et al. |
| 2008/0206799 | A1 | 8/2008 | Blomquist |
| 2008/0215035 | A1 | 9/2008 | Yodfat et al. |

FOREIGN PATENT DOCUMENTS

| | | |
|---|---|---|
| EP | 1 281 351 A2 | 2/2003 |
| EP | 1 571 582 A2 | 9/2005 |
| WO | WO 03/053498 A2 | 7/2003 |
| WO | WO 2004/084820 A2 | 10/2004 |

OTHER PUBLICATIONS

International Search Report, PCT Application No. PCT/IB2008/003185, date of mailing Apr. 9, 2009 and Written Opinion of the International Searching Authority (13 pgs.).
The Diabetes Control and Complications Trial (DCCT) Research Group, "The Effect of Intensive Treatment of Diabetes on the Development and Progression of Long-Term Complications in Insulin-Dependent Diabetes Mellitus", *N Engl J Med* 329: 977-986 (1993).
UK Prospective Diabetes Study (UKPDS) Group, Intensive Blood-Glucose Control with Sulphonylureas or Insulin Compared with Conventional Treatment and Risk of Complications in Patients with Type 2 Diabetes (UKPDS 33), The Lancet 352: 837-853 (1998).
UK Prospective Diabetes Study (UKPDS) Group, "Tight Blood Pressure Control and Risk of Macrovascular and Microvascular in Type 2 Diabetes: UKPDS 38", BMJ 317, (7160): 703-13 (1998).
The Diabetes Control and Complications Trial/Epidemiology of Diabetes Interventions and Complications (DCCT/EDIC) Study Research Group, "Intensive Diabetes Treatment and Cardiovascular Disease in Patients with Type 1 Diabetes", N Engl J Med 353 (25): 2643-53 (2005).
J. Walsh R. Roberts, C.B. Varma and T. Bailey, "Using Insulin, Everything You Need for Success with Insulin" *Torrey Pines Press*, 2003.

*Primary Examiner* — Jon E Angell
(74) *Attorney, Agent, or Firm* — Mintz Levin Cohn Ferris Glovsky and Popeo, P.C.

(57) ABSTRACT

A system and a method for determining an assessed carbohydrate to insulin ratio of a patient is described. The system and the method can comprise a memory component adapted for storing an initial set of values comprising at least one of a blood glucose level, a target blood glucose level, an insulin sensitivity, and, an estimated carbohydrate to insulin ratio. The system and the method can also comprise a bolus selection component adapted for selecting a test bolus corresponding to the determined initial set of values and a planned meal. In one implementation, the bolus selection component can receive bolus dose input from a user. In another implementation, the bolus selection component can estimate the bolus dose using a set of available inputs (e.g. the amount of carbohydrates in the planned meal). The system and the method can further comprise a user interface component adapted for receiving a confirmation that the test bolus has been administered to the patient. In some implementations, the user interface component can be adapted for selecting a meal of a known content.

46 Claims, 14 Drawing Sheets

METHOD AND DEVICE FOR ASSESSING CARBOHYDRATE-TO-INSULIN RATIO

CROSS-REFERENCE TO RELATED APPLICATION

This application claims the benefit of U.S. Provisional Patent Application No, 60/936,690, filed on Jun. 20, 2007, the contents of which are hereby incorporated herein in their entireties by reference.

FIELD OF THE INVENTION

A method and a device for sustained medical infusion of therapeutic fluids to patients is described. Some aspects relate to portable infusion devices and to a method for infusion that includes administering a therapeutic fluid to the patient after assessing a diabetic state of the patient. Some aspects relate to an insulin-dispensing device configured to sense a glucose level in the blood of the patient and to a method for infusing insulin after assessing a carbohydrate-to-insulin ratio ("CIR").

BACKGROUND OF THE INVENTION

Diabetes mellitus is a disease of a major global importance. The number of individuals affected increases at almost epidemic rates, such that in 2006, this number reached approximately 170 million people worldwide and is predicted to at least double over the next 10-15 years. Diabetes is characterized by a chronically raised blood glucose concentration (hyperglycemia), due to a relative or absolute lack of the pancreatic hormone-insulin. Within healthy pancreas, beta cells that are located in the islets of Langerhans and continuously produce and secrete insulin according to the blood glucose levels, thereby maintaining near constant levels of glucose in the body. Long-term tissue complication affects both the small blood vessels (microangiopathy, causing eye, kidney and nerve damage) and the large blood vessels (causing accelerated atherosclerosis, with increased rates of coronary heart disease, peripheral vascular disease and stroke). These complications heavily burden the patients and health care resources that are necessary to treat the patients.

The Diabetes Control and Complications Trial (DCCT) demonstrated that development and progression of chronic complications of diabetes are heavily related to the degree of altered glycemia, as quantified by determinations of glycohemoglobin (HbA1c). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia, which may be accomplished by frequently measuring glucose levels and accordingly adjusting an amount of delivered insulin, is of utmost importance. Conventional insulin pumps can deliver insulin to the patient and can be configured to deliver rapid-acting insulin 24 hours a day through a catheter placed under the skin. The total daily insulin dose can be divided into basal and bolus doses. Basal insulin is delivered continuously over 24 hours and keeps the blood glucose concentration levels (hereinafter, "blood glucose levels") in normal desirable range between meals as well as overnight. Diurnal basal rates can be pre-programmed or manually changed according to various daily activities of the patient. Insulin bolus doses are delivered before or after meals to counteract carbohydrates loads or during periods of high blood glucose concentration levels.

The bullet list below provides a sample of parameters that can be used to select the insulin bolus dose.
- Amount of carbohydrates ("carbs") to be consumed. For example, the amount of carbohydrates can be defined as "servings", wherein 1 serving equals 15 grams of carbohydrates.
- Carbohydrate-to-insulin ratio ("CIR") that represents an amount of carbohydrates balanced by one unit of insulin. CIR can be measured in grams per one unit of insulin.
- Insulin sensitivity ("IS"), i.e., an amount of blood glucose lowered by one unit of insulin. IS can be measured in mg/dL (milligrams/deciliter) per one unit of insulin.
- Current blood glucose levels (CBG). CBG can be measured in mg/dL.
- Target blood glucose levels (TBG), i.e., a desired blood glucose level, which can be measured in mg/dL. TBG for some patients with diabetes is in the range of 90-130 mg/dL before a meal, and less than 180 mg/dL one to two hours after the beginning of a meal.
- Residual insulin (RI), i.e., an amount of stored active insulin remaining in the body of the patient after a recent bolus delivery. For example, this parameter can be relevant when there is a short time interval between consecutive bolus doses (e.g., less than 5 hours).

Conventional insulin pumps require its users to constantly calculate or estimate appropriate pre-meal insulin bolus doses. These calculations or estimations can be based on the above-mentioned parameters, which help provide effective control of the blood glucose levels and, thus, maintenance of normoglycemia. Conventional portable insulin pumps include bolus calculating means that operate based on inputs of meal carbohydrate content and glucose levels by the patient. In these pumps, the calculated bolus dose is automatically calculated and delivered to the patient.

An example of such conventional pumps is discussed in U.S. Pat. No. 6,936,029. An algorithm implemented in the conventional pumps is based on a formula for calculating the recommended bolus dose, depending on the user's IS, CIR, target blood glucose (TBG) and user inputs of BG and Carbs intake. If the current BG is higher than the target BG, the recommended bolus is calculated as follows:

$$\text{recommended bolus} = \underbrace{(TC/CIR)}_{\text{Food Estimate}} + \underbrace{(CBG - TBG)/IS - RI}_{\text{Correction Estimate}} \quad (1)$$

where "TC" is a total amount of carbohydrates; "CIR" is a carbohydrate-to-insulin ratio; "TBG" is a target blood sugar; "CBG" is a current blood sugar; "IS" is an insulin sensitivity; "RI" is a residual insulin.

If the current BG is lower than the target BG, the recommended bolus is calculated as:

$$\text{recommended bolus} = (TC/CIR) + (CBG - TBG)/IS \quad (2)$$

If the current BG is higher than the low target BG and lower than the high target BG (e.g., current blood glucose=105 mg/dL, target blood glucose=90-130 mg/dL) then the recommended bolus is calculated as:

$$\text{recommended bolus} = (TC/CIR) + 0 \quad (3)$$

An accurate assessment of the CIR is essential for determining the recommended bolus dose by the above formulas, and specifically by its "food estimate" portion (See, Equation (1)).

CIR can currently be determined by many type-1 diabetes patients using rapid acting insulin (e.g., Humalog, Novolog) according to the so-called "450 to 500 rules". The patient's CIR can be established by dividing the value corresponding to appropriate "rule" by the total daily dose of rapid-acting insulin. For example, if the total daily insulin dose is 40 Units and the "450 rule" is used, the CIR would approximately equal to 11 grams (i.e., 450 divided by 40).

For example, Table 1 illustrates the Carbs (in grams) covered by 1 Unit of insulin (CIR) according to various "rules". (Table 1 is adapted from Using Insulin, Everything You Need for Success with Insulin, by J. Walsh, R. Roberts, C. B. Varma and T. Bailey, Torrey Pines Press, 2003).

TABLE 1

Carbohydrate-to-insulin ratios according to various "rules", where Carbs are covered by 1 Unit of insulin.

| Total daily insulin dose (TDD) [IU/day] | 500 Rule | 450 Rule |
| --- | --- | --- |
| 20 | 25 | 23 |
| 25 | 20 | 18 |
| 30 | 17 | 15 |
| 35 | 14 | 13 |
| 40 | 13 | 11 |
| 50 | 10 | 9 |
| 60 | 8 | 8 |

The accuracy of the CIR calculated by "rules" is very low because the "rules" are not patient-specific. Additionally, a number of applied "rules" is limited. Thus, for every bolus delivery, an over/under Carbs load-estimation error is further augmented by the inaccuracy of the CIR. The CIR values are often changed, especially in adolescents. Currently, the "rule"-derived CIR value is programmed only once—during the pump initiation. The "rule" is not re-evaluated throughout the usage of the bolus calculator. Thus, a serious hazard of over/under bolus dosing should be further taken into consideration.

Accurate assessments of changes in CIR values over time enable better follow-up and improved glycemic control.

SUMMARY OF THE INVENTION

A system and a method for determining an assessed carbohydrate to insulin ratio of a patient is described. The system and the method can comprise a memory component adapted for storing an initial set of values comprising at least one of a blood glucose level, a target blood glucose level, an insulin sensitivity, and, an estimated carbohydrate to insulin ratio. The system and the method can also comprise a bolus selection component adapted for selecting a test bolus corresponding to the determined initial set of values and a planned meal. In one implementation, the bolus selection component can receive bolus dose input from a user. In another implementation, the bolus selection component can estimate the bolus dose using the available inputs (e.g. the amount of carbohydrates in the planned meal). The system and the method can further comprise a user interface component adapted for receiving a confirmation that the test bolus has been administered to the patient. In some implementations, the user interface component can be adapted for selecting a meal of a known content. For example, a user can select a meal type (e.g. a banana). In some implementations, a user can select the meal type by selecting the meal content (e.g. 24 g of carbohydrates).

The system and the method can further comprise a blood glucose sensing component adapted for determining a post-bolus blood glucose level of the patient. The system and the method can also comprise a CIR assessment component adapted for determining the assessed carbohydrate to insulin ratio of the patient based on the initial set of values and the post-bolus blood glucose level value.

In one implementation, if a difference in blood glucose values calculated by subtracting the initial blood glucose level value from the post-bolus blood glucose level value is less than a predefined absolute value, then the assessed carbohydrate to insulin ratio can be determined to be substantially the same as the initial carbohydrate to insulin ratio of the patient.

In another implementation, if a difference in the blood glucose values calculated by subtracting the initial blood glucose level value from the post-bolus blood glucose level value is greater than a predefined value, the user interface component is further adapted for advising the patient to administer a correction bolus.

In yet another implementation, if a difference in the blood glucose values calculated by subtracting the post-bolus blood glucose level value from the initial blood glucose level value is greater than a predefined value, the user interface component is further adapted for advising the patient to consume an amount of carbohydrates to achieve the target blood glucose level.

The user interface component can be adapted for advising the patient to fast for a period of time prior to determining the initial set of values. For example, the period of time can be longer than five hours.

The user interface component can further be adapted for advising the patient to achieve normoglycemia prior to determining the initial set of values. The user interface component can further be adapted for advising the patient to achieve normoglycemia after the confirmation that the test bolus has been administered is received.

In one variation, the determination of normoglycemia can be made by comparing the post-bolus blood glucose level of the patient to the target blood glucose level. In one implementation, while the normoglycemia is not achieved, the user interface component can be adapted for repetitively requiring the patient to perform a glucose correction. For example, the blood glucose sensing component can retest the post-bolus blood glucose level of the patient after each glucose correction. In one variation, the glucose correction can comprise at least one of the administering a correction bolus and consuming a correction glucose.

In one implementation, the assessed carbohydrate to insulin ratio can be determined based on the correction bolus. The assessed carbohydrate to insulin ratio can also be determined based on the correction glucose. In one implementation the user interface can further be adapted for requiring the patient to perform the glucose correction during a predetermined period of time.

In one variation, the system for determining the carbohydrate to insulin ration can further comprise an insulin infusion component coupled to said blood glucose sensing component. The insulin infusion component can be configured as a patch unit adherable to the skin of the patient.

The system can further comprise a remote control unit configured to communicate with the patch unit and further configured to allow programming and data acquisition. In some implementations, the CIR assessment component can reside in the remote control unit.

In one variation, the blood glucose sensing component can be a glucose monitor. The glucose monitor can be a glucometer or, in some implementations, a CGM.

In some implementations, the device can be configured to continuously monitor body glucose levels and simultaneously deliver insulin bolus doses to the body of the patient based on the assessed patient's CIR-values. The device can be miniature, discreet, economical and cost-effective. A system can also be provided that includes a miniature patch, that is securable to the skin of the patient and that can continuously dispense insulin based on the assessed patient's CIR-values.

A device that includes an insulin patch unit configured to assess patient's CIR values and that includes a disposable part and a reusable part is also described. The reusable part can be configured to include relatively expensive components and the disposable part is configured to include relatively cheap components. The patch unit can also be configured to continuously monitor insulin and glucose levels in the patient.

In some implementations, a described device can be configured to include an insulin infusion patch unit that can be remote-controlled and capable of assessing patient's CIR-values. The patch unit can also be configured to continuously monitor insulin and glucose levels in the patient.

In some implementations, the CIR-value assessment feature can be implemented in a device that is configured as remote-controlled insulin infusion patch unit. It can also be implemented in a remote unit of an insulin dispensing device.

DETAILED DESCRIPTION OF THE EMBODIMENTS

Figure 1A:
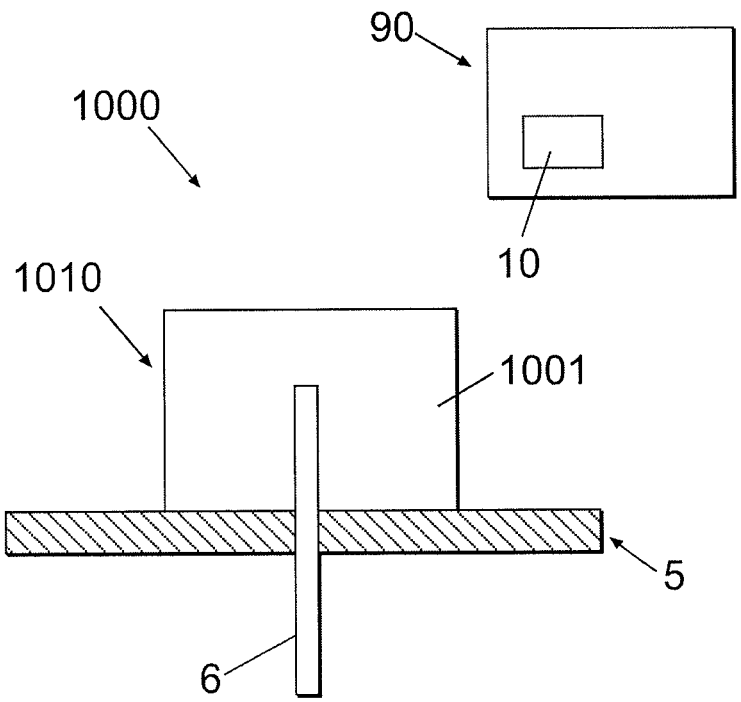
FIGS. 1a-b illustrate some examples of the devices that can implement the CIR assessment feature.

A system and a method for determining an assessed carbohydrate to insulin ratio of a patient is described. The system and the method can comprise a memory component adapted for storing an initial set of values comprising at least one of a blood glucose level, a target blood glucose level, an insulin sensitivity, and, an estimated carbohydrate to insulin ratio.

The system and the method can also comprise a bolus selection component adapted for selecting a test bolus corresponding to the determined initial set of values and a planned meal. The system and the method can further comprise a user interface component adapted for receiving a confirmation that the test bolus has been administered to the patient. The system and the method can further comprise a blood glucose sensing component adapted for determining a post-bolus blood glucose level of the patient. The system and the method can also comprise a CIR assessment component adapted for determining the assessed carbohydrate to insulin ratio of the patient based on the initial set of values and the post-bolus blood glucose level value.

In some implementations, the CIR-value assessment can be carried out according to the following steps that can be performed in any suitable order:

1. Prior to assessing CIR-values of the patient, the patient may be required to fast and rest for a period of time (e.g., 5 hours). During this period, any influence of residual insulin can be substantially eliminated.
2. During a first blood glucose ("BG") measurement step, patient's BG is sensed and measured ($CBG_0$).
3. During a contemplated Carb in-taking step, the patient may contemplate to consume a snack that contains known amount of carbohydrates of a high glycemic index (e.g., a marketed bag of pretzels). The glycemic index ("GI") is a ranking system for carbohydrates based on their effects on blood glucose levels in the first two hours. The snack should not be a high-fat or high-protein food (which can take longer to digest and are slower to affect BG).

Table 2 below illustrates few examples of recommended foods and their GIs.

| Classification | GI range | Examples |
|---|---|---|
| Low GI | 55 or less | most fruit and vegetables (but not potato), oats, buckwheat, whole barley, All-bran |
| Medium GI | 56-69 | sucrose, basmati rice |
| High GI | 70 or more | cornflakes, baked potato, jasmine rice, white bread, white rice, Mars bar |

4. During bolus administering step, normal insulin bolus (as opposed to the extended bolus) is being administered to the patient, according to the contemplated Carb intake. The administered bolus is calculated using the Carb load divided by the currently applied CIR-values (i.e., bolus=Carb/current CIR values).
5. During a Carb in-taking step, the patient can consume the contemplated snack from step (3).
6. In the next step, consecutive BG measurements can be observed until at least two consecutive BG measurements are approximately the same ($CBG_1$), that is ±Ymg/dL (e.g. Y=10 mg/dL), or until the duration of insulin action (e.g. 3 hours) has elapsed. In one implementation, the time between BG measurements can be 10-30 minutes.
7. The difference between $CBG_1$ and $CBG_0$ can be calculated and the CIR-value can be re-evaluated accordingly.

In some implementations, the patient can avoid additional food intake or bolus insulin delivery during the above test. In some implementations, the above test should not be carried out during a stressed condition (e.g., illness, menses, etc.) because of increased basal requirements that could alter the accuracy of CIR-values assessment. In some implementations, if a glucose level substantially returns to its initial value (i.e. $BG_0$), then the current CIR value can be adequate. If glucose level doesn't return to it's initial value (i.e. $BG_0$), then the current CIR value ("$CIR_{old}$") can be inadequate and a new CIR value ("$CIR_{new}$") can be calculated according to a formula discussed below and applied.

According to one embodiment, if $CBG_1-CBG_0 > Y$ mg/dL (Y being a relatively small number, e.g. 10 mg/dL) then:

$$CIR_{New} = \frac{CIR_{Old} * Carb}{carb + CIR_{Old} * \frac{CBG - TBG}{IS}} \quad (4)$$

In one implementation, if $CBG_1>TBG$ a correction bolus can be administered according to the following equation: $(CBG_1-TBG)/IS$ wherein $CBG_1$ is the blood glucose at the end of the test, TBG is the target BG, IS is the user's insulin sensitivity. According to one embodiment, if $CBG_1 - CBG_0 < -Y$ mg/dL (Y being a relatively small number, e.g. 10 mg/dL) then $$CIR_{new} = \frac{Carb}{\frac{carb}{CIR_{old}} - \frac{\Delta BG}{IS}} \quad (5)$$

wherein $\Delta BG = CBG_0 - CBG_1$

According to such an embodiment, if $CBG_1<TBG$ correction carbs(CC) is to be consumed according to the following equation:

$$CC = (CIR_{new}(TBG-BG1))/IS \quad (6)$$

According to the assessed $CIR_{new}$ value, the pump's CIR value setting can be set by a caregiver (e.g., nurse, physician) or by the patient and further bolus doses can be administered according to $CIR_{new}$.

In some embodiments, the new CIR value can be automatically re-set without involvement of user interface, and further bolus doses can be administered according to the new CIR. According some embodiments, the pump can be configured to remind the patient to perform a CIR value assessment test periodically or at every predetermined period of time (e.g., each month). According to some embodiments, the pump may remind the user to perform a CIR value assessment test more frequently if there is significant variability in the CIR values between previous tests.

In some implementations, the CIR assessment capability can be implemented in an insulin infusion device. In other embodiments, the CIR assessment capability can be implemented in a glucose monitoring device. In yet other embodiments, the CIR assessment capability can be implemented in a device that can be configured to deliver insulin and monitor glucose levels and that can be further configured to deliver insulin automatically or semi-automatically based on the sensed glucose levels (for example, in a closed, a semi-closed or an open-loop system).

In some embodiments, the CIR value assessment can be implemented in an insulin infusion device having an insulin dispensing patch unit and a remote control unit, wherein a glucose sensing apparatus (e.g., glucometer) can be integrated in the remote control unit. In some embodiments, the dispensing patch unit may be composed of two parts: a reusable part that includes all electronic and driving components (i.e., relatively expensive components) and a disposable part that includes insulin reservoir (and other cheap components).

The glucose sensing apparatus can be alternatively be integrated in the reusable part of the device. In some embodiments, the CIR assessment capability could be implemented in the remote control unit of the insulin infusion device. Alternatively, the CIR assessment capability could be implemented in the reusable part of the device.

In some embodiments, the CIR assessment capability can be implemented in the dispensing patch unit that continuously senses and monitors body glucose concentration levels and can concomitantly deliver insulin into the body. The dispensing patch unit may include a reusable part and a disposable part. The insulin-dispensing and glucose-sensing capabilities can be combined into a semi-closed loop system, where a processor-controller apparatus controls the dispensing of basal insulin according to the sensed glucose concentration.

In some embodiments, the CIR assessment capability is implemented in the remote control unit of the device. Alternatively, this capability could be implemented in the reusable part of dispensing patch unit of the device. Alternatively, the CIR assessment capability could be implemented in both the reusable part of the dispensing patch unit of the device and the remote control unit of the device.

Figure 1B:
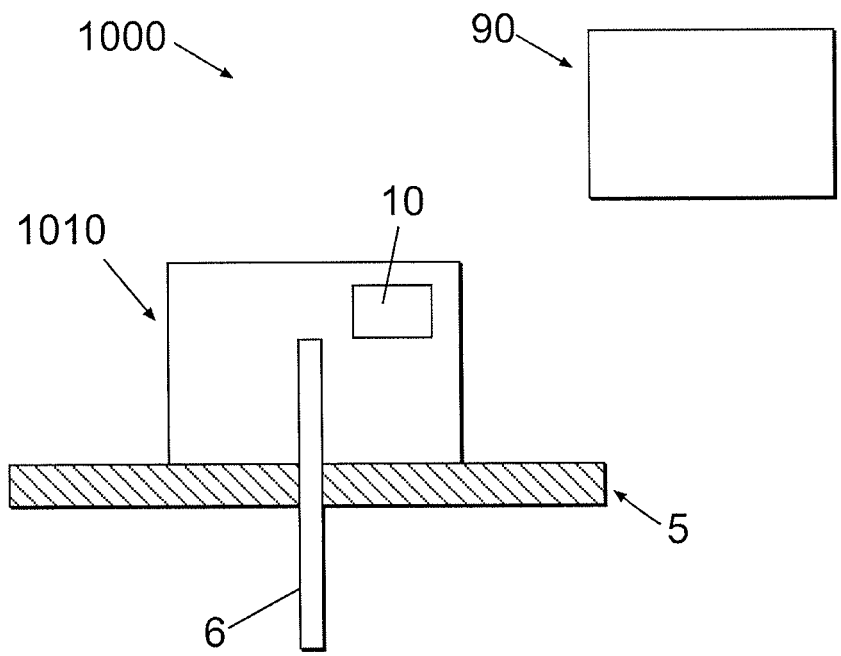

FIGS. 1a and 1b illustrate embodiments of a device (1000) for dispensing a therapeutic fluid in a patient, e.g., insulin in a diabetes patient. The device (1000) includes an insulin infusion unit (1010), that can be configured as a pump, a separate glucose measurement unit (e.g., glucometer) (90), and a CIR assessment feature (10). According to some embodiments of the device, the insulin infusion pump unit (1010) can be configured to include a cannula (6) that penetrates the skin (5) to allow delivery of insulin to the patient. In FIG. 1a, the CIR assessment feature (10) is located in the insulin infusion pump unit (1010). In FIG. 1b, the CIR assessment feature (10) is located in the glucose measurement unit (90). According to some embodiments, the insulin infusion pump unit communicates with a remote control unit allowing programming, user inputs and data acquisition. In still further embodiment of the system the CIR assessment feature may be located in the remote control unit. According to some embodiments, the glucometer is not a separate item but can be retrofitted within the insulin infusion pump unit or it may be installed in the remote control unit. As can be understood by one skilled in the art, other embodiments of the device, in which the CIR assessment feature may be located either in the glucometer, the pump unit, the remote control unit or anywhere else are possible.

According to some embodiments, the device can be configured to include an insulin infusion pump, a continuous glucose measurement (CGM) item, and a CIR assessment feature. In this embodiment the CIR assessment feature may be located in either the pump or the CGM item.

In some implementations, the insulin infusion pump unit can be configured to include a continuous glucose measurement ("CGM") item. In these embodiments, the infusion pump and the CGM may be located in the same housing and may communicate with a remote control unit. A CIR assessment feature may be located either in the CGM, the pump unit, or in the remote control unit.

Figure 2A:
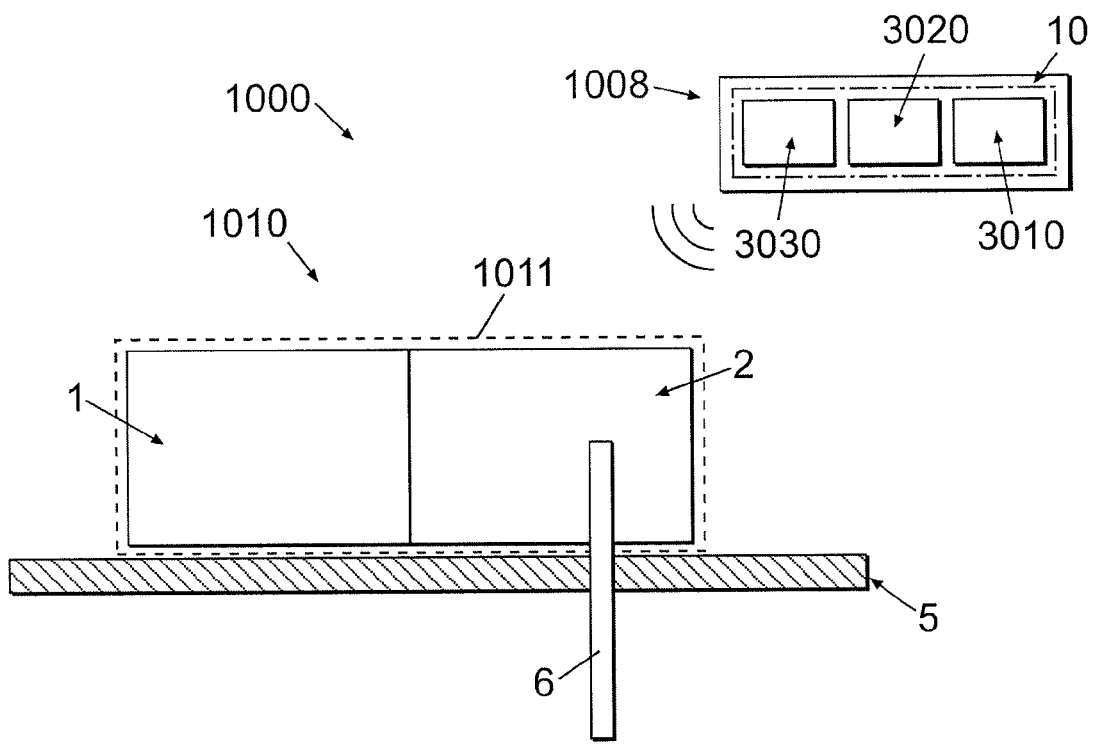
FIGS. 2a-b illustrate exemplary insulin infusion devices having an insulin dispensing unit and a remote control unit that contains one implementation of the CIR assessment feature.
Figure 2B:
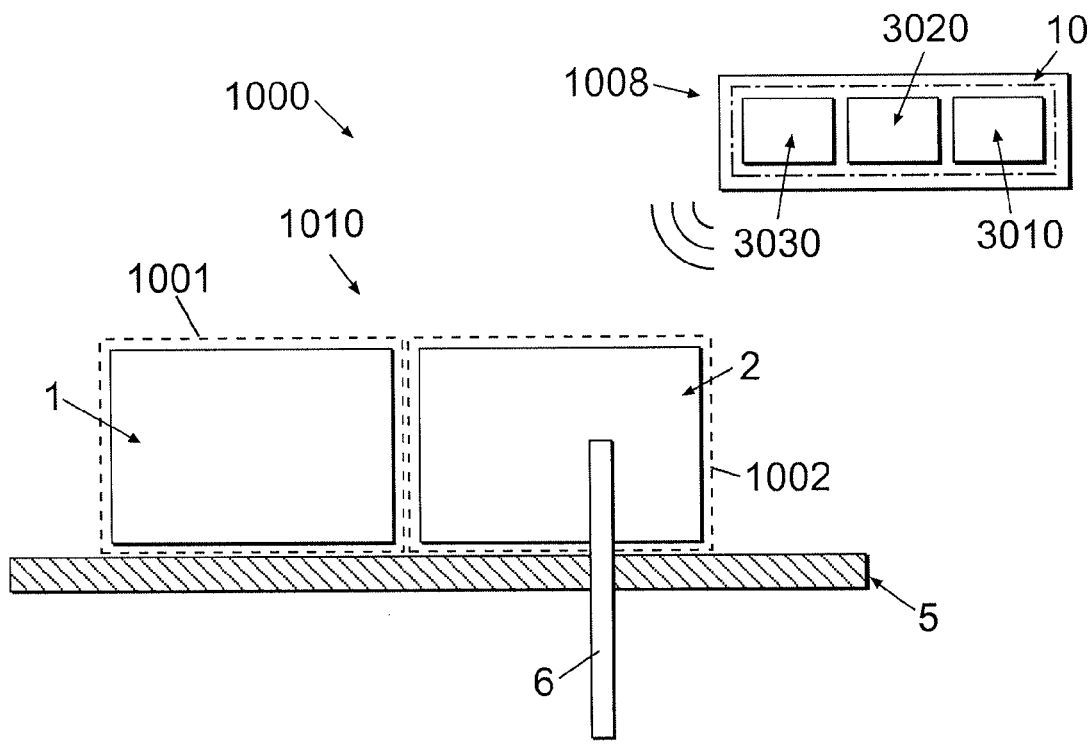

FIGS. 2a and 2b illustrate exemplary embodiments of a device, in which an insulin infusion pump (1010) is configured as a patch unit that can be adhered to the user's skin (5). The system includes a remote control unit (1008) that communicates with the patch unit allowing programming, user inputs and data acquisition.

Manual inputs can be effectuated by buttons (not shown in FIGS. 2a-b) located on the patch unit. The patch unit can be configured to include one housing as shown by the dotted line (1011) in FIG. 2a. Alternatively, the patch unit can be configured to include two housings (1001, 1002) that are configured as reusable part (1) and disposable part (2), respectively, as shown in FIG. 2b.

In some embodiments, the patch unit can be configured to include a cannula (6) that penetrates the skin (5) to allow delivery of insulin to the patient. The patch unit (110) can be configured to be directly attached to the user's skin by an adhesive (not shown in FIGS. 2a-b). Alternatively, it can be configured to be attached to a dedicated cradle unit (not shown in FIGS. 2a-b) that is adherable to the user's skin (5) and allow connection/disconnection of the patch unit (1010). An exemplary embodiment of this arrangement is discussed in a co-owned, co-pending U.S. Provisional Patent Application No. 60/876,679, the disclosure of which is incorporated herein by reference in its entirety.

In some embodiments, the remote control unit (1008) can be configured to include the CIR assessment feature (10) that has a processor (3010), an input means (3020) and a display (3030). The input means (3020) allows programming of the CIR assessment feature (10). The input means (3020) also can be used for programming of the patch unit (1010). The remote control unit (1008) can be configured to include an announcement means (for example, a speaker, a vibrating element, a flash indicator, or any other suitable device).

Figure 3A:
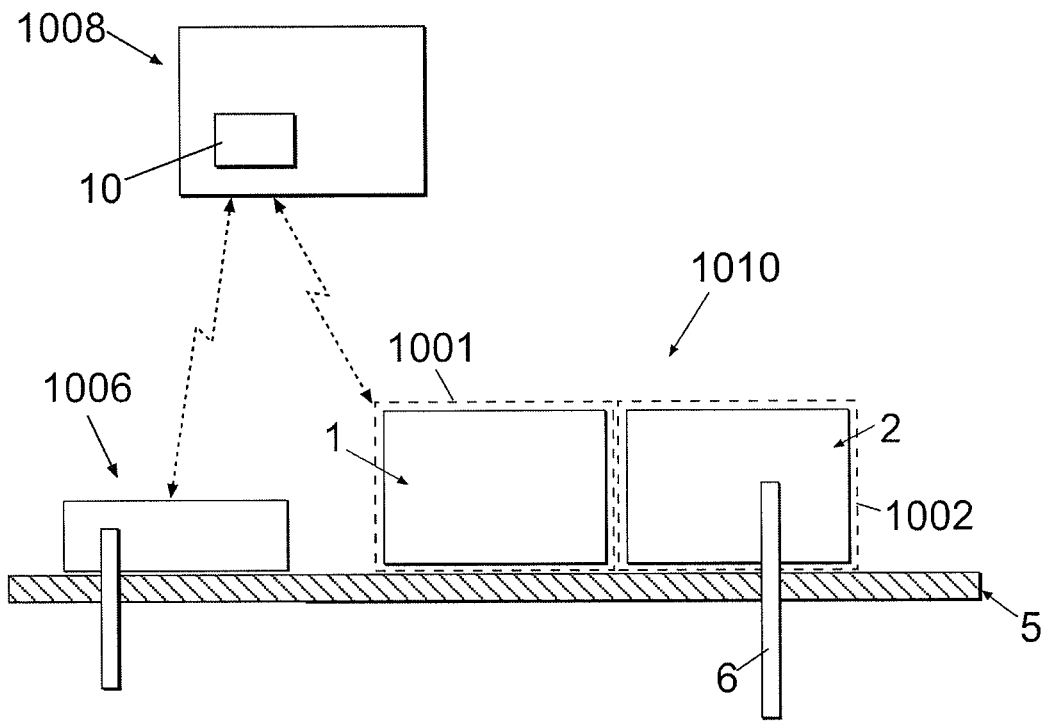
FIGS. 3a-b illustrate exemplary insulin infusion devices including continuous subcutaneous glucose monitors that are configured to provide blood glucose readings for some implementations of the CIR assessment feature.
Figure 3B:
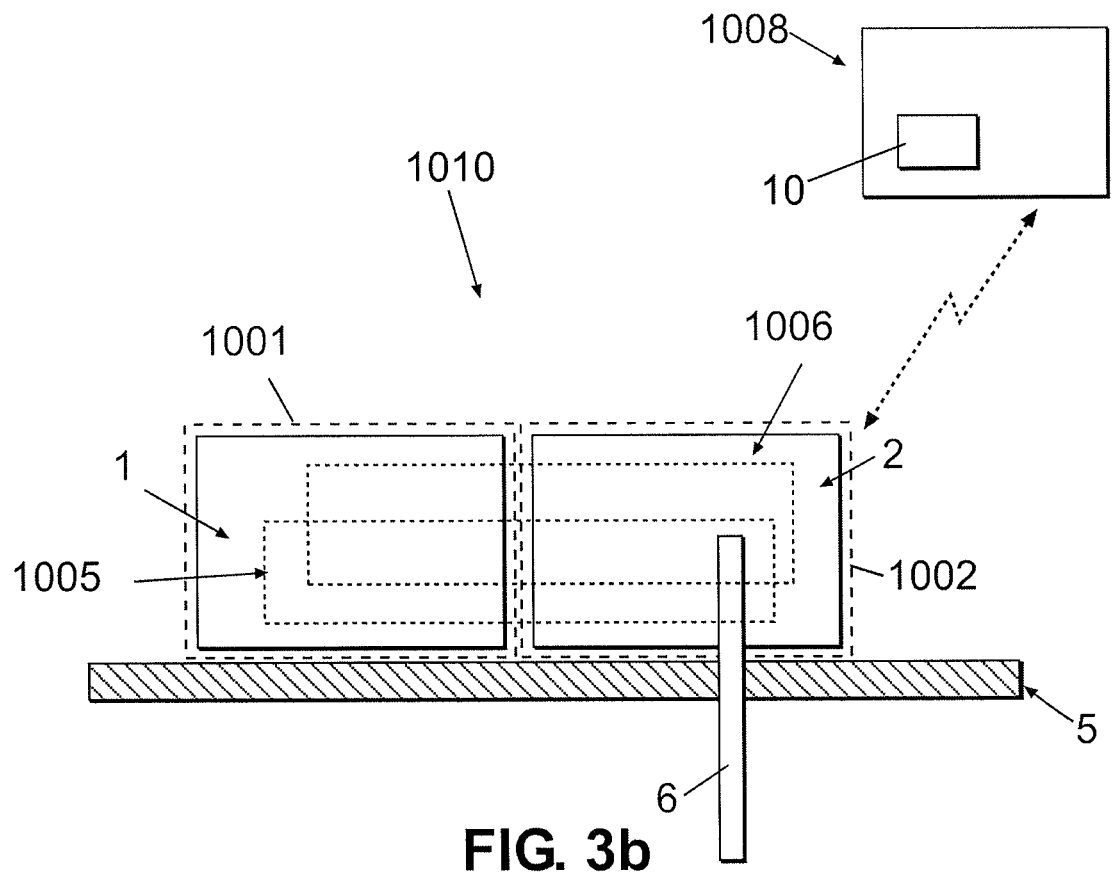

FIGS. 3a and 3b illustrate exemplary embodiments in which blood glucose readings (that are supplied to the CIR assessment feature (10)) are received from a dedicated and continuous subcutaneous glucose monitor (1006). A communication channel can be configured to connect the glucose monitor (1006) and the CIR assessment feature (10). In some embodiments, the communication channel can be configured to reside in the remote control unit (1008) and can further be configured to allow programming, data handling, and user inputs.

FIG. 3a illustrates an exemplary embodiment, in which the current blood glucose (BG) is measured by an independent continuous subcutaneous glucose monitor (1006). FIG. 3b illustrates an exemplary embodiment, in which the continuous subcutaneous glucose sensing monitor (1006) is integrated within the patch unit of the insulin delivery device.

The insulin infusion device in the embodiment of FIG. 3b can be configured to include a dispensing apparatus (1005) and glucose sensing monitor (1006) that can be further configured to constitute a single delivery device. This delivery device can be configured to use a single cannula (6) shared by both dispensing and sensing apparatus. An exemplary embodiment of this apparatus is further discussed in the co-owned, co-pending U.S. patent application Ser. No. 11/706,606, the disclosure of which is incorporated herein by reference in its entirety. In some embodiments, the sensing apparatus and the dispensing apparatus can be configured to have separate cannulae that penetrate the skin (5) and reside in the subcutaneous tissue. The insulin infusion device of these embodiments can be configured to include two parts—a reusable part (1) and a disposable part (2) that correspond to housing (1001, 1002), respectively.

In some embodiments, the insulin infusion device may function in a closed loop or semi closed loop mode. Insulin can be automatically dispensed according to a continuous monitoring of glucose concentration levels (using a closed-loop mode) or according to a continuous monitoring and additional pre-meal bolus patient-inputs (using a semi-closed loop mode). The CIR assessment feature (10) can be also incorporated in this embodiment and used for calculation of the bolus inputs when the system functions in a semi-closed loop mode.

Figure 4:
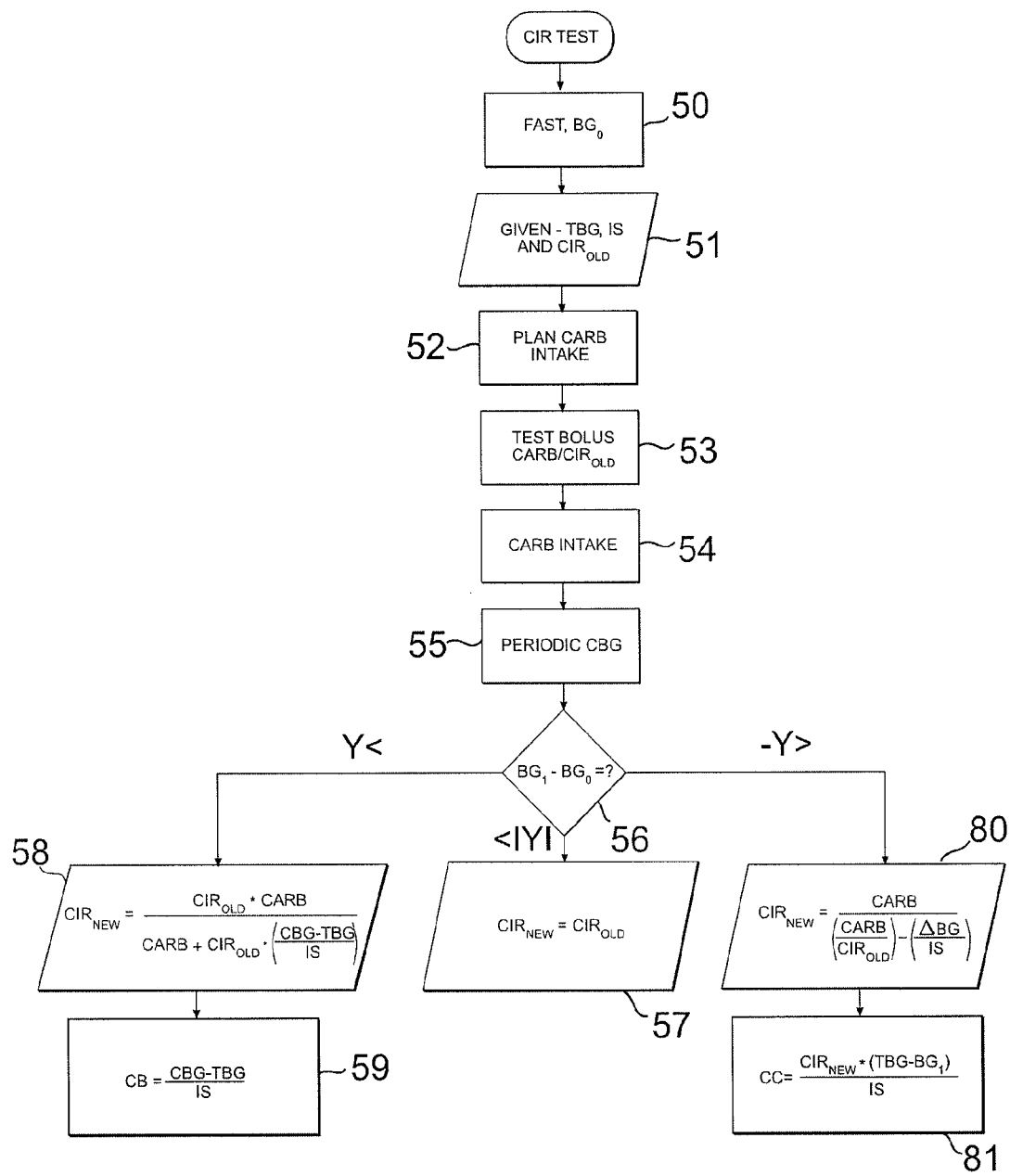
FIG. 4 is an exemplary block diagram representing a sample algorithm that can be used by the CIR assessment feature.

FIG. 4 is an exemplary flow chart representing a method for assessing CIR values that can be implemented in the CIR assessment feature. The method includes several steps representing a test procedure in which BG of the patient can be sensed and measured and the CIR can be calculated. The steps can be performed either in the order presented or in any other suitable order. In some embodiments, the method begins with a step (50), where the user may be required to fast and avoid strenuous physical activity for a specified period of time (e.g., 5 hours) prior to the beginning of the test procedure. This allows previous boluses to be substantially eliminated. At the end of the fasting period the BG is measured ($BG_0$). This BG measurement serves as the baseline BG value for the test.

Further, the method can involve use of three patient parameters: a range of TBG (e.g., 80 mg/dL-120 mg/dL), IS and $CIR_{old}$ which is the Carbohydrate-to-Insulin Ratio that is known prior to carrying out the test procedure. This is shown in step (51). The method then can proceed to step (52), where the patient contemplates to consume a meal with a known amount of carbohydrates, and preferably with a high glycemic index (e.g., an energy bar). In step (53), a normal insulin bolus can be administered to the patient. The normal insulin bolus can be calculated based on the previously known CIR, i.e., Bolus=Carbs/$CIR_{old}$. The method then can proceed to step (54), where the patient consumes the contemplated meal from step (52). The method then can proceed to step (55), where current BG levels ("CBG") are sensed and measured periodically (e.g., every 15 minutes) until at least two measurements are approximately the same, "$BG_1$" (e.g. ±10 mg/dL). Alternatively, at least 1 BG measurement can be carried out after the duration of insulin action (user specific, e.g. 4 hours) has elapsed. The difference between "$BG_1$" and "$BG_0$" can then be calculated, see step (56).

If the difference between "$BG_1$" and "$BG_0$" is smaller than the absolute value of a certain predefined "Y" (e.g. Y=15 mg/dL), than:

$$CIR_{new} = CIR_{old} \qquad (7)$$

That is, there is no change in the user's CIR value.

If the difference between "$BG_1$" and "$BG_0$" is larger than a certain predefined "Y" (e.g. Y=15 mg/dL), than not enough insulin was administered at step (53) because the currently applied CIR value is too high. A new, smaller, CIR value is calculated, see step (58), according to the following equation:

$$CIR_{New} = \frac{CIR_{Old} * Carb}{carb + CIR_{Old} * \frac{CBG - TBG}{IS}} \qquad (8)$$

If the user is not euglycemic (i.e. low TBG<$BG_1$<high TBG), then the user can be recommended to administer a correction bolus that can bring him/her to target BG range, see step (59). The correction bolus can follow the formula:

$$CB = (CBG_1 - TBG)/IS \qquad (9)$$

If the difference between "$BG_1$" and "$BG_0$" is smaller than a certain predefined "−Y" (e.g. Y=−15 mg/dL), then, it is possible that too much insulin was administered at step (53) because the currently applied CIR value is too small. A new, higher, CIR value can be calculated, see step (80) according to the following equation:

$$CIR_{new} = \frac{Carb}{\frac{carb}{CIR_{old}} - \frac{\Delta BG}{IS}} \quad (10)$$

If the user is not euglycemic (i.e. low TBG<$BG_1$<high TBG), than the user is recommended to consume carbohydrates ("CC") that will bring him/her to target BG range, see step (81). The correction bolus follows the formula:

$$CC = (CIR_{New}(TBG - BG_1))/IS \quad (11)$$

In some implementations, a continuous glucose monitoring device ("CGM") can be used in conjunction with the CIR assessment feature. In these embodiments, glucose measurements can be continuously carried out by the CGM device, thereby making periodic measurements redundant.

Figure 5:
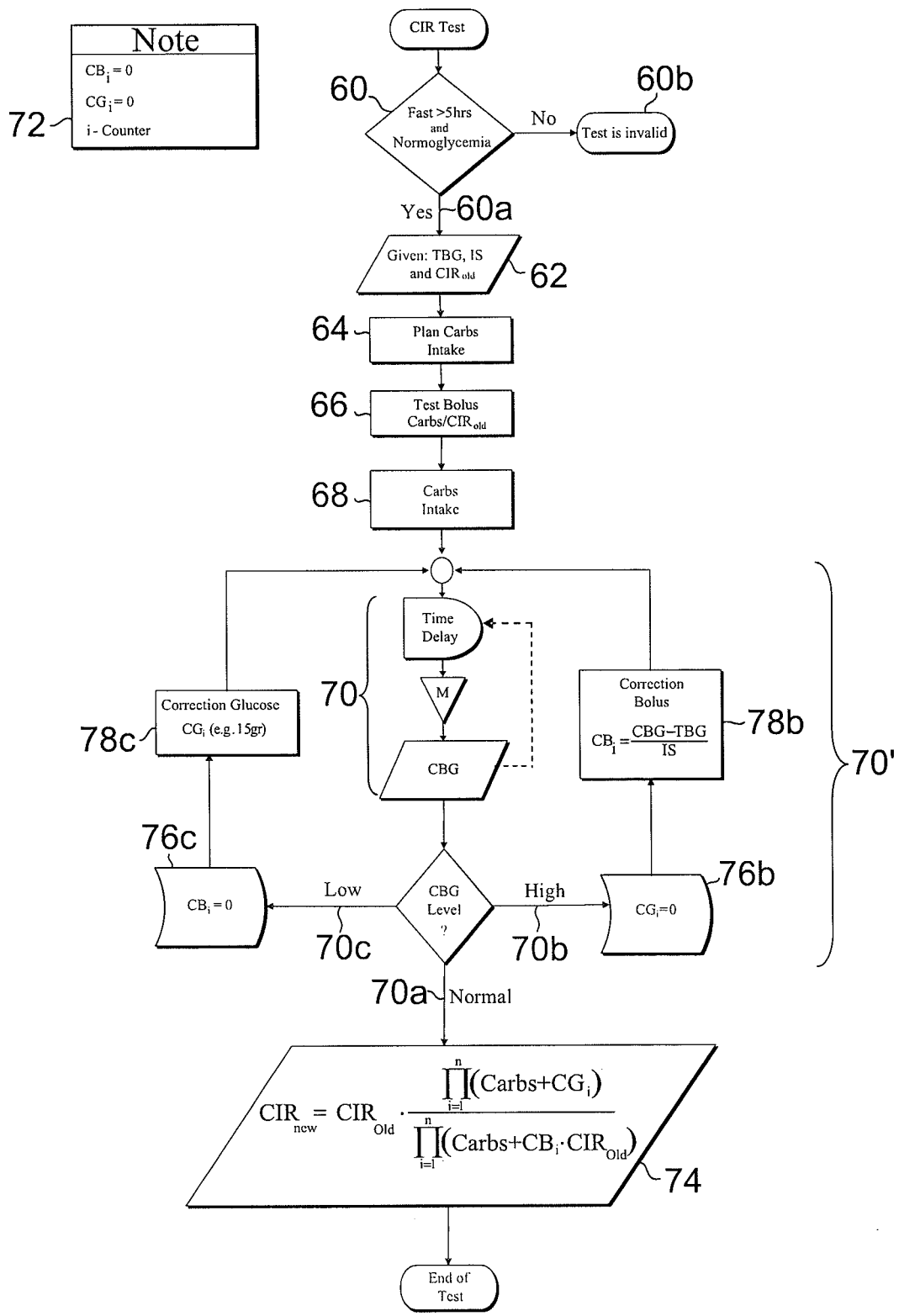
FIG. 5 is another exemplary block diagram representing another algorithm that can be used by the CIR assessment feature.

FIG. 5 is another exemplary flow chart representing a method for assessing CIR values that can be implemented in the CIR assessment feature. The method can include several steps representing a test procedure in which BG of the patient can be sensed and measured and the CIR can be calculated. In some embodiments, the method can begin with a step (60), where the user may be required to fast and avoid strenuous physical activity for a specified period of time (e.g., at least 5 hours) prior to the beginning of the test procedure. This can allow the patient to be brought under a normoglycemia state, that is, patient's current blood glucose level ("CBG") can satisfy the following condition (low TBG)<CBG<(high TBG), as shown by arrow (60a). If this condition is not fulfilled, the method may not proceed further and can be terminated, as designated by a numeral (60b). The patient may be required to fast for the predetermined period of time (e.g., at least 5 hours) so that the patient can be brought up to a normoglycemia state.

Further, the method can involve use of three patient parameters, for example: a range of TBG (e.g., 80 mg/dL-120 mg/dL), IS and CIRoId which is the Carbohydrate-to-Insulin Ratio that is known prior to carrying out the test procedure. This is shown in step (62). The method then can proceed to step (64), where the patient can plan to consume a meal with a known amount of carbohydrates, and preferably with a high glycemic index (e.g., an energy bar). In step (66), a normal insulin bolus can be administered to the patient. The normal insulin bolus can be calculated based on the previously known CIR, i.e., Bolus Carbs/$CIR_{old}$. The method then can proceed to step (68), where the patient can consume the meal planned at step (64). The method can proceed to step (70), where current BG levels ("CBG") can be sensed and measured periodically (e.g., every 15 minutes). In some embodiments, these measurements can be carried out during a certain test time limit (e.g., 2-3 hours). For simplicity of explanation, each such period will be designated by a counter "i" while a total number of periods used for CIR determination will be designated by "n".

In some implementations, if the CBG measurement shows normoglycemia (as illustrated by step (70a)) after a single BG observation (n=1), the assignment of the initial parameters (72) ($CB_1$ and $CG_1$ i.e. initial correction bolus and initial glucose correction, respectively) in the CIR formula (as shown in step (74)) can mean that the CIR values do not change ($CIR_{new} = CIR_{old}$).

Since n=1, the initial parameters (72) $CB_1$ and $CG_1$ (both are assigned to be zero) are substituted into the formula shown in step (74):

$$\forall n = 1: CIR_{new} = CIR_{old} \cdot \frac{\prod_{i=1}^{n}(Carbs + CG_i)}{\prod_{i=1}^{n}(Carbs + CB_i \cdot CIR_{old})} \quad (12)$$

$$= CIR_{old} \cdot \frac{Carbs + 0}{Carbs + 0}$$

$$= CIR_{old}$$

resulting in $CIR_{new} = CIR_{old}$.

In some implementations, if the CBG level is above the target zone (TBG) (this is shown by step (70b)), then the $CG_i$ can be assigned to zero, as shown in step (76b), and a correction bolus can be administered to the patient, as shown in step (78b). For example, the correction bolus can be calculated according to the formula:

$$CB_i = \frac{CBG - TBG}{IS} \quad (13)$$

In some implementations, if the CBG level is below the target zone (TBG) (this is shown in step (70c)), then the $CB_i$ can be assigned as zero, as shown in step (76c), and a glucose correction, for example, 15 g of Carbs, can be administered to the patient, as shown in step (78c). In some implementations, the above steps, commonly designated by a numeral 70', may be repeated several times until normal BG level is achieved, as shown by step (70a) and the values of $CB_i$ and $CG_i$ are stored in memory (e.g., CPU). When the CBG value achieves a level corresponding to normoglycemia (shown by step (70a)), the stored data ($CG_i$ and CBS) can be extracted and substituted in to the formula shown in step (74) for the purposes of re-evaluation of $CIR_{new}$ values, according to the following formula:

$$CIR_{new} = CIR_{old} \cdot \frac{\prod_{i=1}^{n}(Carbs + CG_i)}{\prod_{i=1}^{n}(Carbs + CB_i \cdot CIR_{old})} \quad (14)$$

where Carbs is the consumed amount of carbs (as shown in step (68)) and $CI_{old}$ is the CIR known before the CIR test.

In some embodiments, if at beginning of this method (i.e., i=1) the CBG is greater than TBG, then $CG_1 = 0$ and $CB_1$ can be calculated according to the formula (II) also shown in step (78b). Thus, $CB_1 = 15$ Units. Assuming that after the next group of measurements (as shown by a group of steps (70)), the patient's BG level is still not in the target zone and is lower then TBG, a glucose correction is administered to the patient, as shown in step (78c). Thus, $CB_2 = 0$ and $CG_2 = 15$ g. If the patient's BG level is in the target zone, as shown in step (70a), the CIR value can be re-assessed, according to the formula shown in step (74) as follows:

$$\forall n = 2: CIR_{new} \quad (15)$$

$$= CIR_{old} \cdot \frac{\prod_{i=1}^{n}(Carbs + CG_i)}{\prod_{i=1}^{n}(Carbs + CB_i \cdot CIR_{old})}$$

$$= CIR_{old} \cdot \frac{(Carbs + CG_1) \cdot (Carbs + CG_2)}{(Carbs + CB_1 \cdot CIR_{old}) \cdot (Carbs + CB_2 \cdot CIR_{old})}$$

$$= \_$$

$$= CIR_{old} \cdot \frac{(Carbs + 0) \cdot (Carbs + CG_2)}{(Carbs + CB_1 \cdot CIR_{old}) \cdot (Carbs + 0)} =$$

$$= CIR_{old} \cdot \frac{Carbs + CG_2}{Carbs + CB_1 \cdot CIR_{old}}$$

Based on the above, $CIR_{new}$ value can be calculated since all members of the formula given above are now known.

In some embodiments, a continuous glucose monitoring device ("CGM") can be used in conjunction with the CIR assessment feature. In these embodiments, glucose measurements can be continuously carried out by the CGM device, thereby making periodic measurements redundant. In some embodiments, the CGM device may alarm the patient or any other user of the system when the CBG value enters and/or exits the target zone during the CIR assessment test.

Figure 6A:
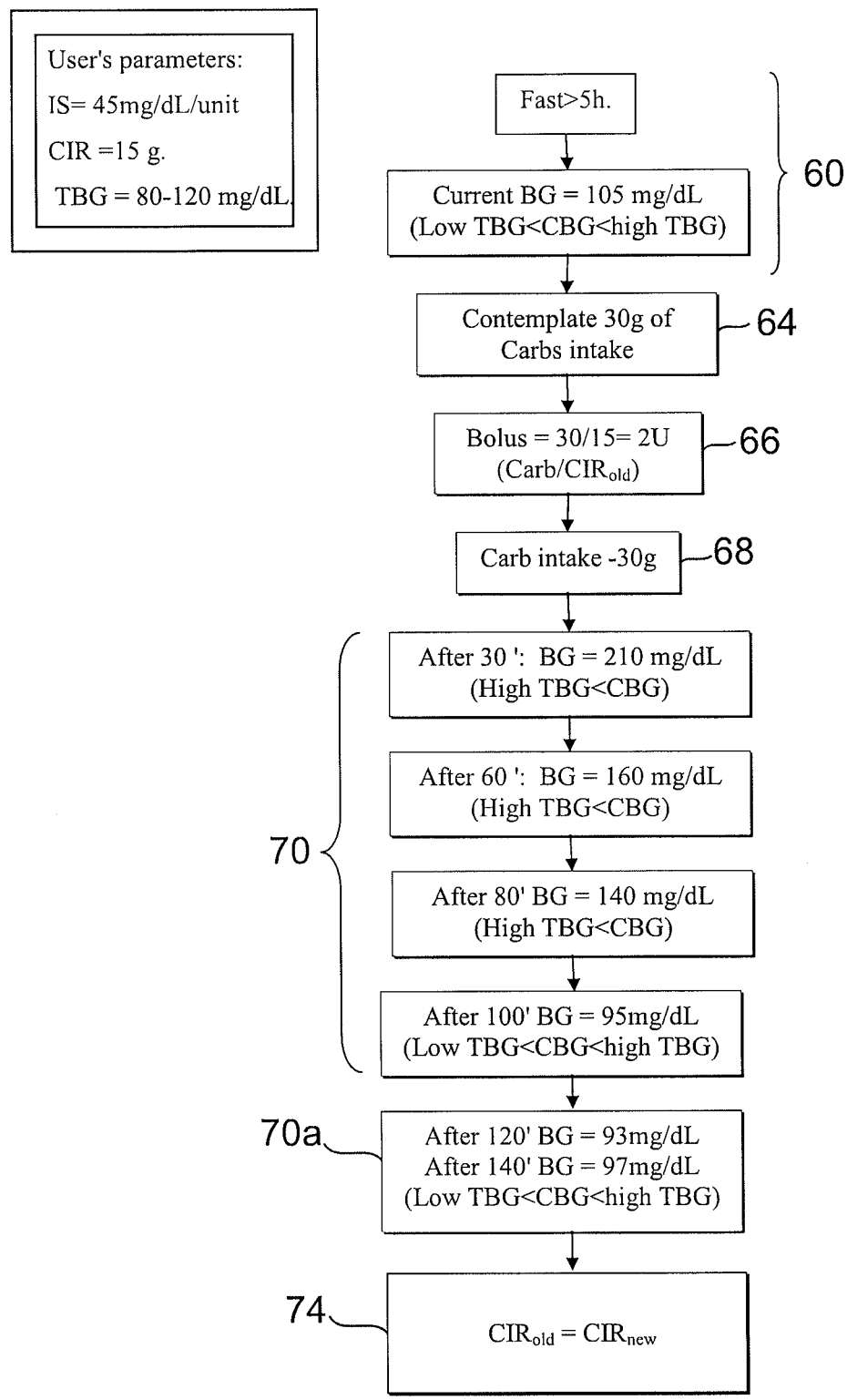
FIGS. 6a-b provide a sample CIR assessment algorithm and a sample diagram of the blood glucose values over time.

FIG. 6a is an exemplary flow chart illustrating a method of assessing CIR values, according to the algorithm depicted in FIG. 5, in a situation when the blood glucose returns to the normal level within the predetermined time limit (e.g., 3 hours). In this exemplary embodiment, IS=45 mg/dl/unit, CIR=15 grams, and TBG is in the range of 80-120 mg/dL. According to this example, the following steps can be carried out in any suitable order:
1. Patient fasts and rests for five hours (step (60)).
2. CIR value can be assessed, for example, when the measured fasting glucose equals to 105 mg/dL, which falls in the target zone (step (60)).
3. The patient plans to consume an energy bar (or any other type of food containing designated dosage of carbohydrates), which has 30 grams of carbohydrates (step (64)).
4. A normal insulin bolus of 2 U can be administered to the patient (step (66)) (based on the contemplated carbs intake).
5. The patient can consume the contemplated carbs intake having 30 g of carbohydrates (step (68)).
6. Blood glucose (BG) can be observed every 30 minutes during the first hour, and every 20 minutes thereafter until normoglycemia is reached (step (70)). In this example, normoglycemia can be achieved after 100 minutes (which is within the time limit of the test).
7. Two additional consecutive BG measurements are carried out to ensure that hypoglycemia does not occur and that the patient's BG levels remain within the target zone, i.e., normoglycemia is maintained.
8. Normoglycemia can be maintained (step (70a)), which means that the current CIR value can be adequate and should not be changed (step (74)).

Figure 6B:
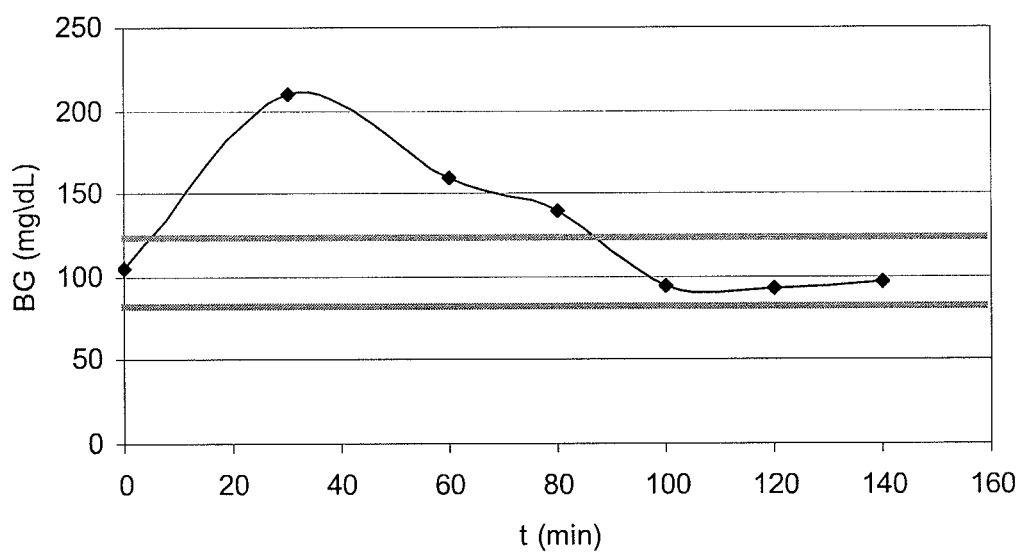

FIG. 6b is an exemplary plot that illustrates sample patient's observed BG values over time. In the beginning when t=0, the patient consumes the above referenced carbs load. When CGM device is used in conjunction with the CIR assessment feature, the BG can be measured more frequently (e.g., every 5 minutes). In FIG. 6b, two horizontal gray lines represent the target zone's boundaries associated with a particular patient (80 mg/dL<BG<120 mg/dL). Such boundary lines of the target zone can be set based on a specific patient.

Figure 7A:
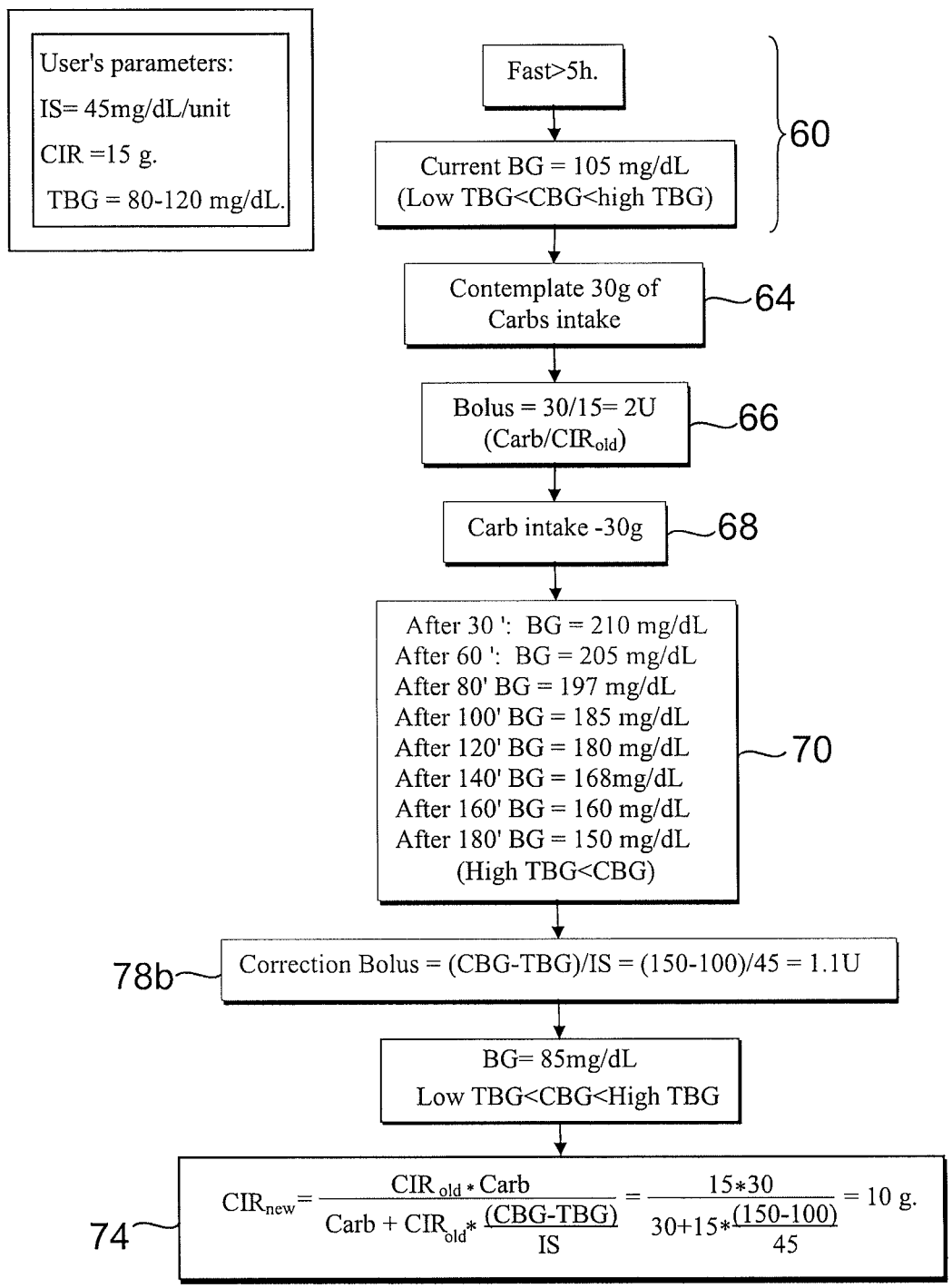
FIGS. 7a-b is an exemplary CIR assessment algorithm for a situation in which the blood glucose remains high after the predefined period of time.

FIG. 7a is an exemplary flow chart illustrating an example of the method for assessing CIR value according to the algorithm depicted in FIG. 5, in a situation when the blood glucose level remains high after the predetermined test's time limit has passed (e.g., 2 hours). The following parameters are applicable in this example: IS=45 mg/dl/unit, CIR=15 g, and TBG is in the range of 80-120 mg/dL. Based on these parameters, the following steps can be carried out in any suitable order:
1. The patient fasts and rests for at least five hours (step (60)).
2. CIR value can be assessed when the measured fasting glucose equals to 105 mg/dL, which falls within the target zone (step (60)).
3. The patient can plan to consume an energy bar (or any other food) that has 30 g of carbohydrates (step (64)).
4. A normal insulin bolus of 2 U can be administered to the patient based on the carb intake (step (66)).
5. The patient can consume the planned carb intake having 30 g of carbohydrates (step (68)).
6. Blood glucose (BG) is observed every 30 minutes during the first hour, and every 20 minutes thereafter until the time limit of the test has passed (3 hours) (step (70)).
7. A correction bolus of 1.1 U can be administered to the patient (step (78b)), according to the following calculation:

$$(CBG-TBG)/IS=(150-100)/45=1.1 \text{ U} \quad (16)$$

8. Once normoglycemia is achieved, while the BG is periodically measured, the prior CIR value ($CIR_{old}$) can be re-evaluated by the CIR assessment feature and a new CIR ($CIR_{new}$) can be calculated (step (74)), for example, according to the following:

$$CIR_{new} = \frac{CIR_{old} * carb}{carb + CIR_{old} * \frac{(CBG - TBG)}{IS}} \quad (17)$$

$$= \frac{15 * 30}{30 + 15 * \frac{(150 - 100)}{45}}$$

$$= 10 \text{ g}$$

Figure 7B:
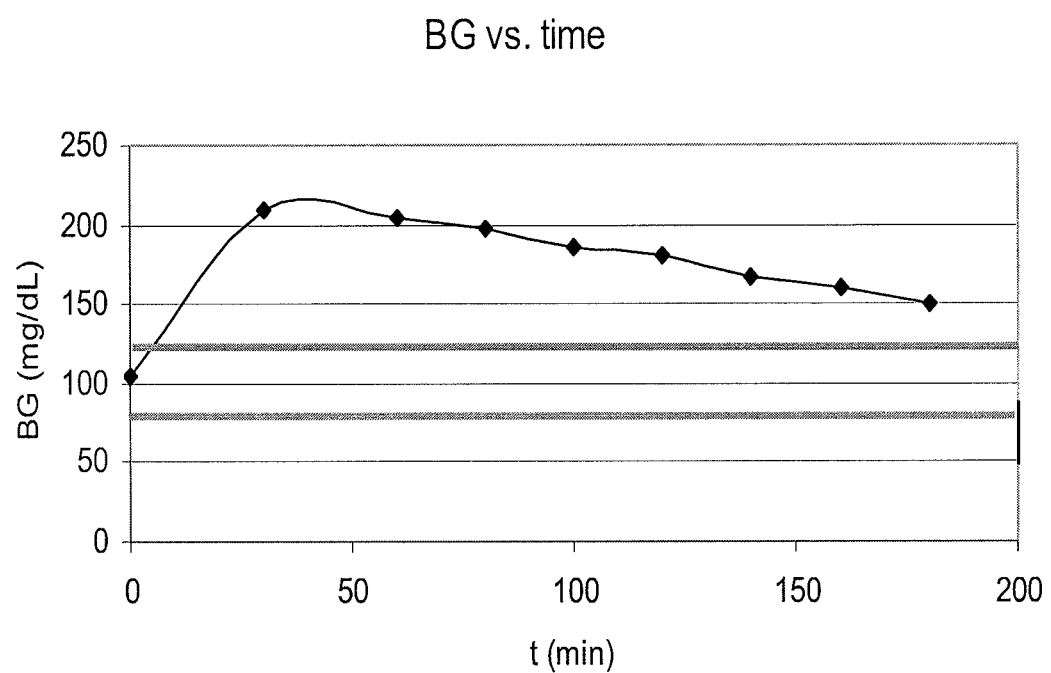

FIG. 7b illustrates an exemplary plot of patient's BG values over time. For example, in the beginning, when t=0, the patient can consume the carbohydrate load. By the end of the test's time limit, the patient can become hyperglycemic, thus, a correction bolus can be administered and a new CIR can be determined. In FIG. 7b, two horizontal gray lines can represent target zone boundaries associated with a particular patient (80 mg/dL<BG<120 mg/dL).

Figure 8A:
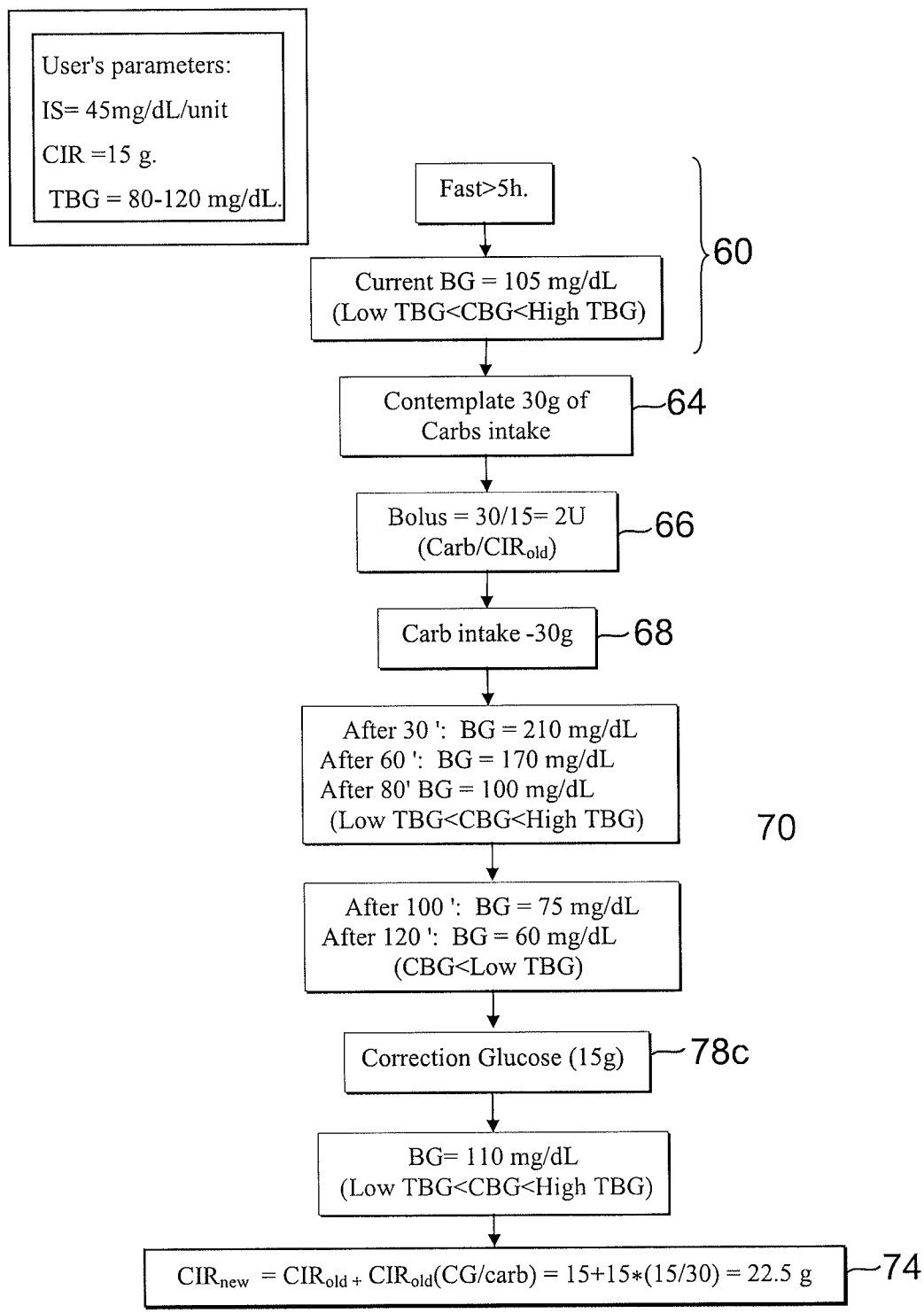
FIGS. 8a-b is an exemplary CIR assessment algorithm for a situation in which normoglycemia is reached before the predefined period of time has expired, but hypoglycemia is presented in subsequent measurements.

FIG. 8a is an exemplary flow chart illustrating a method of assessing CIR values, according to the algorithm depicted in FIG. 5 in a situation when normoglycemia is reached prior to the expiration of the test's time limit, but hypoglycemia is presented as follows from subsequent BG measurements. The following parameters are applicable in this example: IS=45 mg/dl/unit, CIR=15 g, and TBG is in the range of 80-120 mg/dL. According to the example, the following steps are carried out:
1. The patient can fast and rest for five hours (step (60)).
2. CIR value can be assessed when the measured fasting glucose equals to 105 mg/dL, which falls within the target zone (step (60)).
3. The patient can plan to consume an energy bar that includes 30 grams of carbohydrates (step (64)).
4. A normal insulin bolus of 2 U can be administered to the patient (step (66)) (according to the carbs intake).

5. The patient can consumes the planned carb intake having 30 g of carbohydrates (step (68)).
6. Blood glucose (BG) can be measured every 30 minutes during the first hour, and every 20 minutes thereafter until normoglycemia is reached (step (70)).
7. Two additional consecutive BG measurements can be carried out, which provide evidence that hypoglycemia occurs.
8. The patient can consume a correction glucose carbohydrates dose of 15 g (e.g., tablespoon of honey) (step (78c)).
9. Normoglycemia can be established (i.e., patient's BG level is within the target zone).
10. The prior CIR value ($CIR_{old}$) can be re-evaluated (step (74)) and a new CIR value ($CIR_{new}$) can be calculated according to the following:

$$CIR_{new}=CIR_{old}+CIR_{old}(CG/carb)=15+15*(15/30)= 22.5 \text{ g} \qquad (18)$$

Figure 8B:
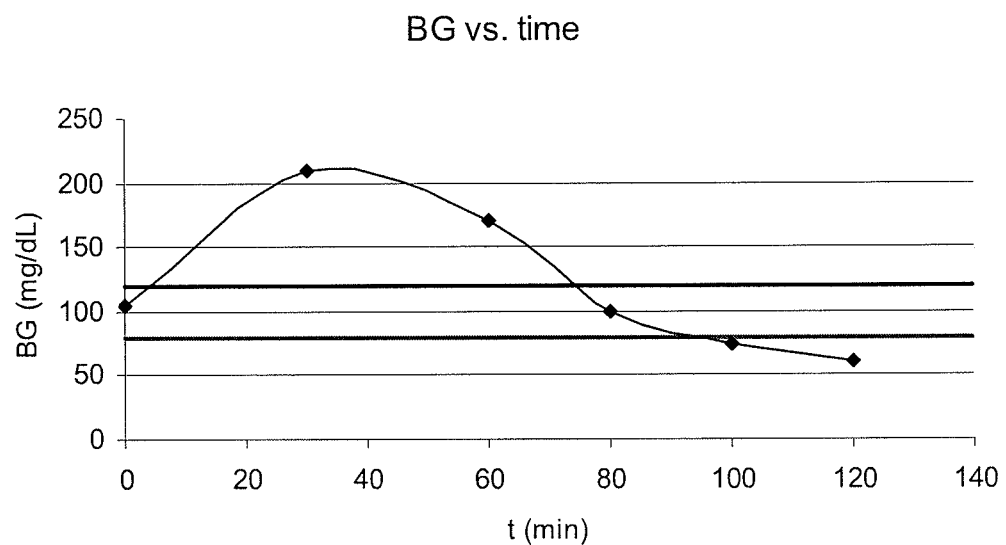

FIG. 8b illustrates an exemplary plot of the user's BG values over time. In the beginning when t=0, the patient can consume a carbs load. The patient can reache normoglycemia prior to the expiration of the test's time limit (3 hours), however, hypoglycemia can occur as evidenced by the results of the measurements in step 7 above. The patient can consume a corrective carbs dose and a new CIR value can be determined. In FIG. 8b, two horizontal gray lines represent the target zone boundaries associated with a particular patient (80 mg/dL<BG<120 mg/dL).

Figure 9A:
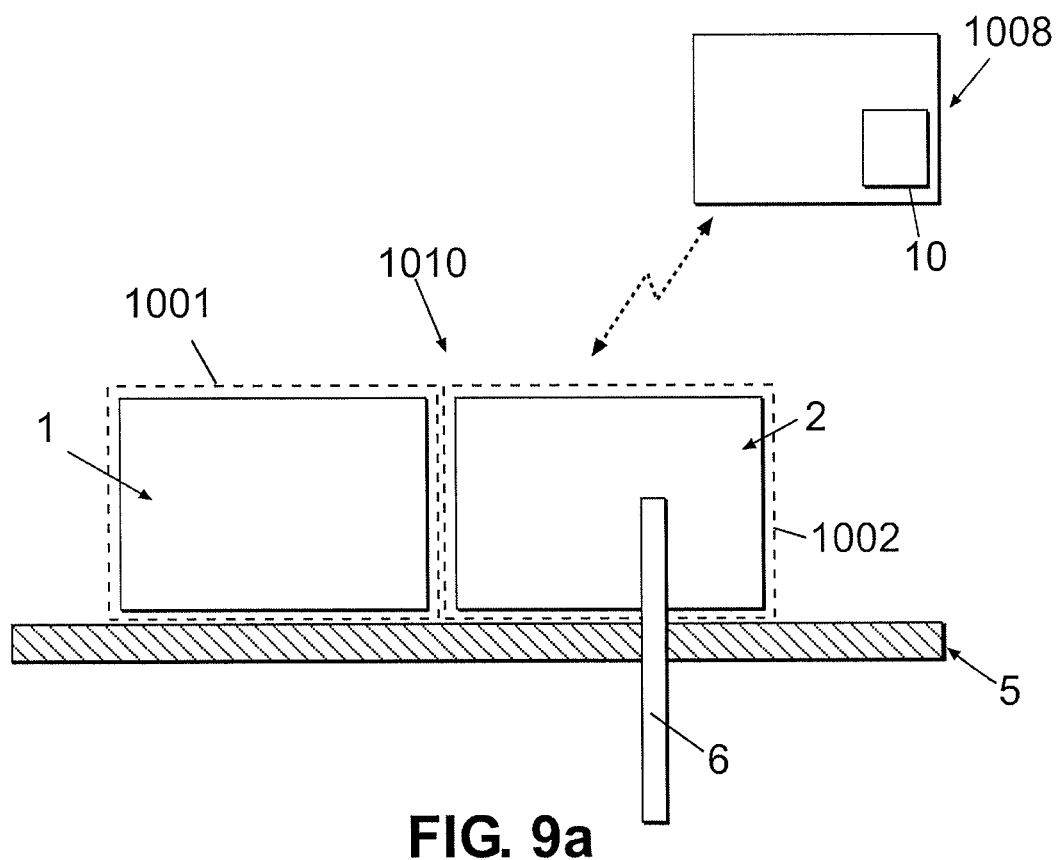
FIGS. 9a-b illustrate exemplary insulin infusion devices provided with the CIR assessment feature.
Figure 9B:
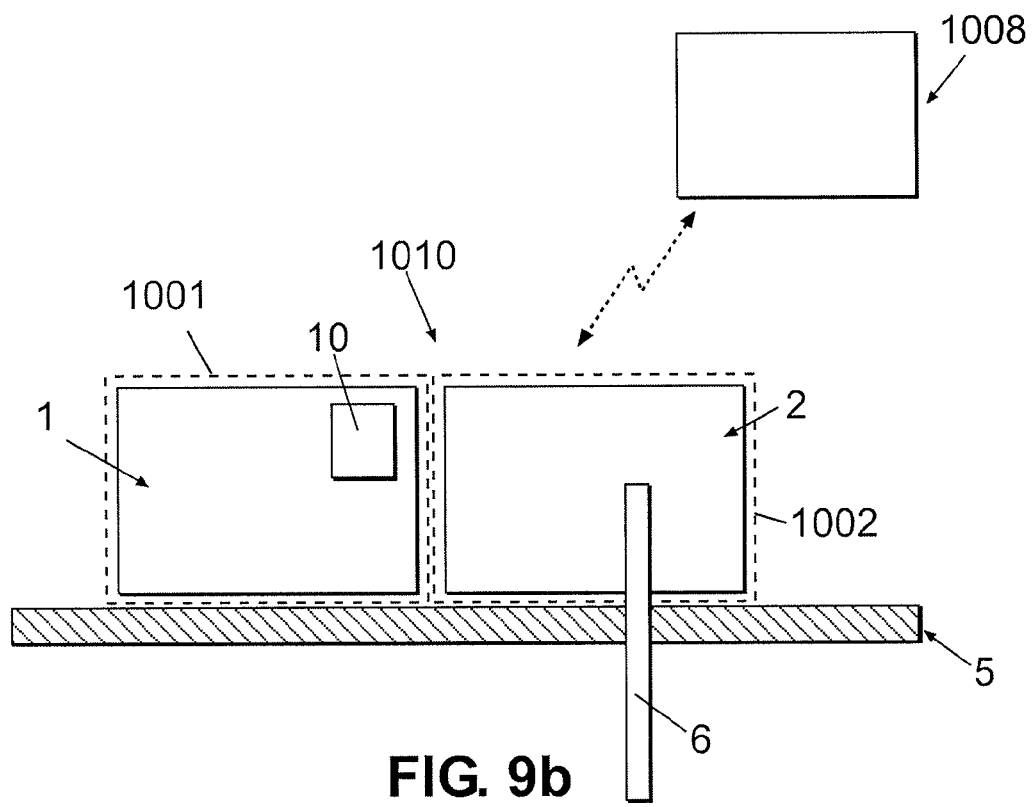

FIGS. 9a and 9b illustrate exemplary embodiments of the system in which the insulin delivery device can be configured as the patch unit (1010) having two parts located in two separate housings (1001, 1002). The parts of the patch unit are—a reusable part (1) and a disposable part (2). The relatively cheap components of the device reside in the disposable part (2) (e.g., cannula (6)) and the relatively expensive components reside in the reusable part (1). In other exemplary embodiments, the cannula (6) can be attached to a skin adhered cradle unit allowing the connection and disconnection of the patch unit.

In some embodiments, the system can be configured to include a remote control unit (1008) and a CIR assessment feature (10). In some embodiments, the CIR assessment feature can include memory, database, processor, source of energy, and input/output interface. Programming of the patch unit can be carried out by a remote control unit or by dedicated buttons (not shown in FIG. 9) provided on the patch unit. In FIG. 9a, the CIR assessment feature (10) is configured to be located in the remote control unit (1008). In FIG. 9b, the CIR assessment feature (10) is configured to be located in the reusable part (1) of the patch unit (1010).

Figure 10A:
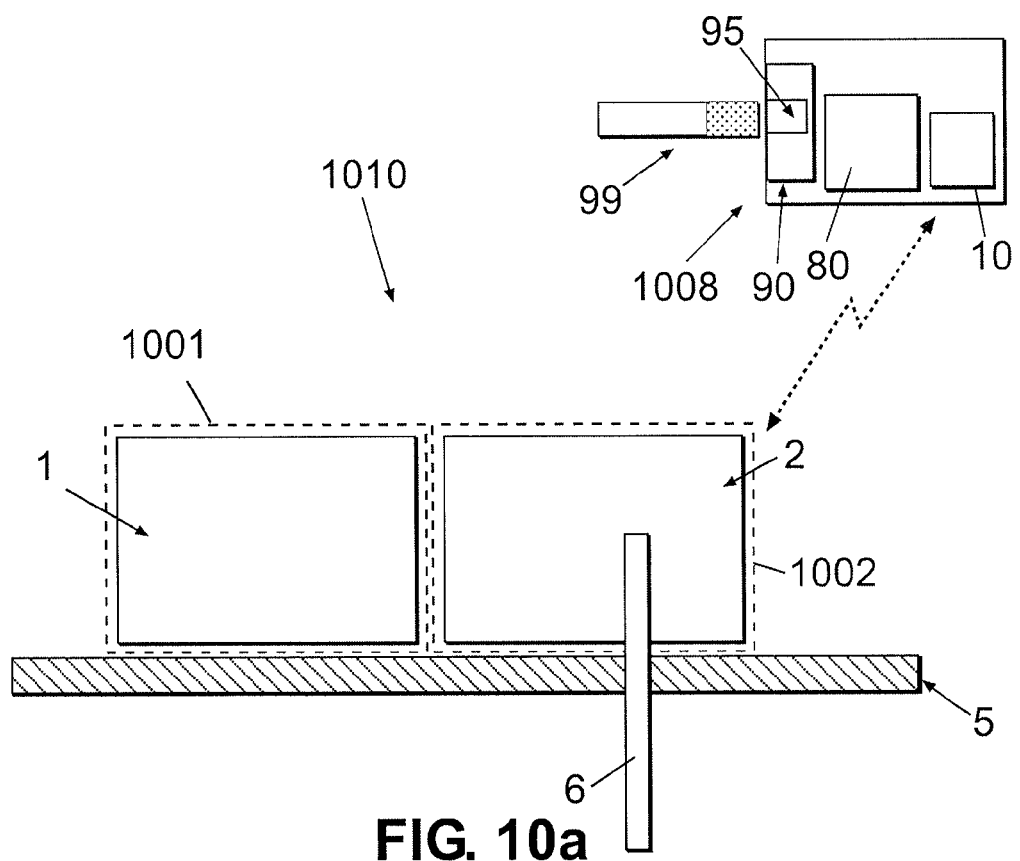
FIGS. 10a-c illustrates exemplary insulin infusion devices having blood glucose monitors deployed in three sample locations for providing blood glucose (BG) readings to the CIR assessment feature.
Figure 10B:
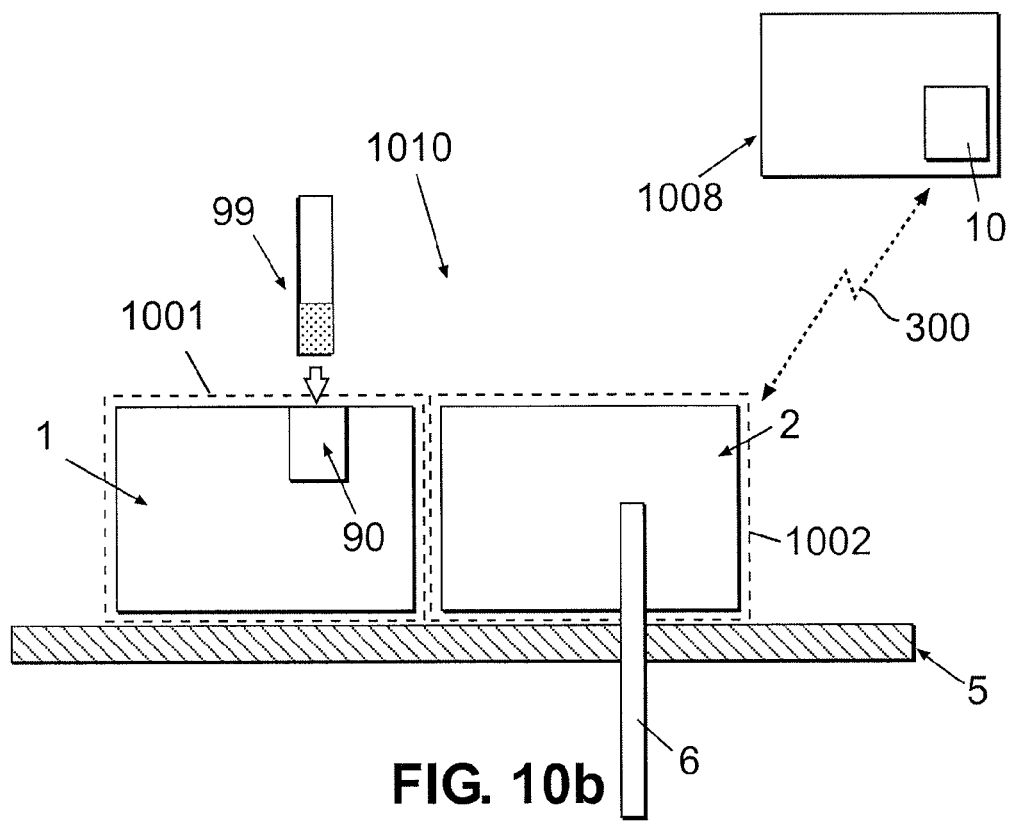
Figure 10C:
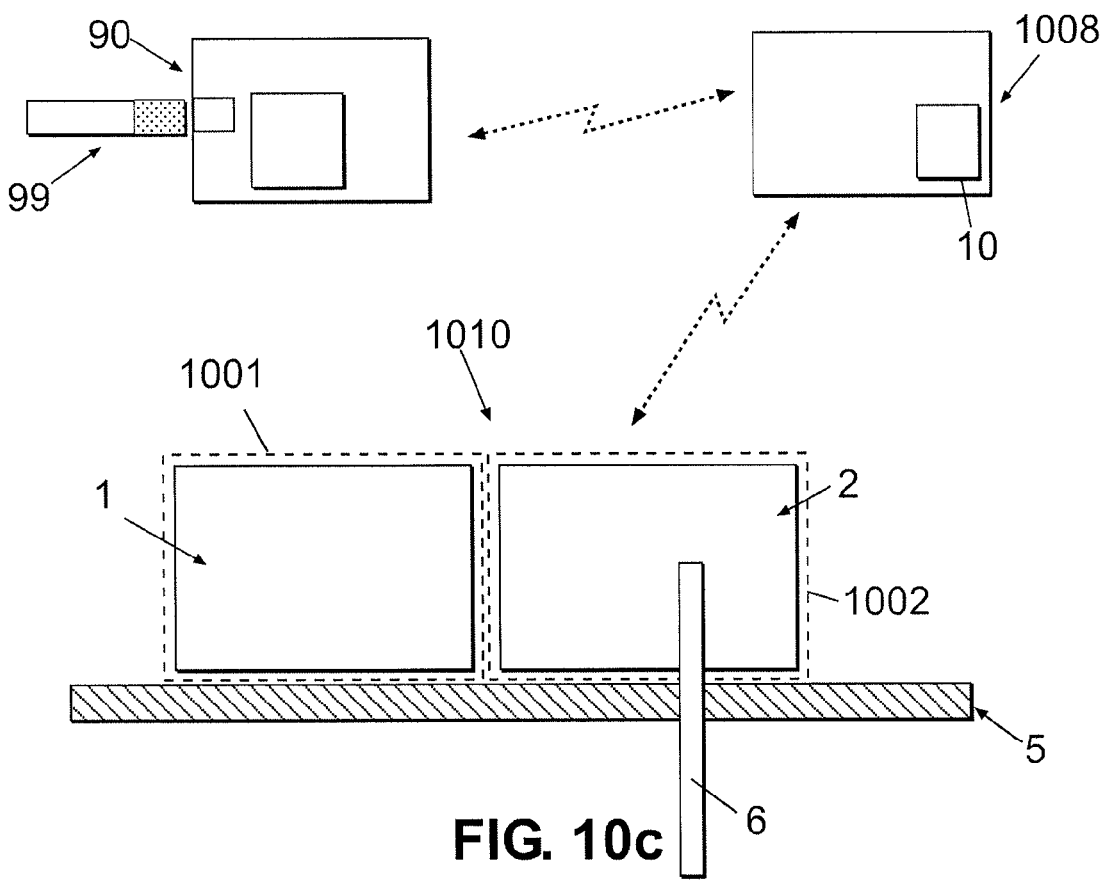

FIGS. 10a, 10b and 10c illustrate three exemplary embodiments of the insulin delivery device, each containing a glucometer (90). The glucometer (90) can be used for acquiring blood glucose (BG) values inputted to the CIR assessment feature (10).

FIG. 10a illustrates a glucometer (90) located in the remote control unit (1008) of the device. In this embodiment, the glucometer (90) includes an opening (95) for receiving of a test strip (99). The patient can extract blood from the body, place a blood drop on the test strip (99) and insert the test strip into the opening (95). The glucose readings are displayed on a screen (80) of the remote control unit (1008). FIG. 10b illustrates a glucometer (90) located in the reusable part (1) of the patch unit (1010). A communication channel (300) is configured to connect the glucometer (90) residing in the patch unit (1010) and the CIR assessment feature (10) residing in the remote control unit (1008). The communication channel is configured to allow programming, data handling, and user inputs. FIG. 10c illustrates an exemplary embodiment in which glucose readings are (90) received from an independent glucometer.

Figure 11:
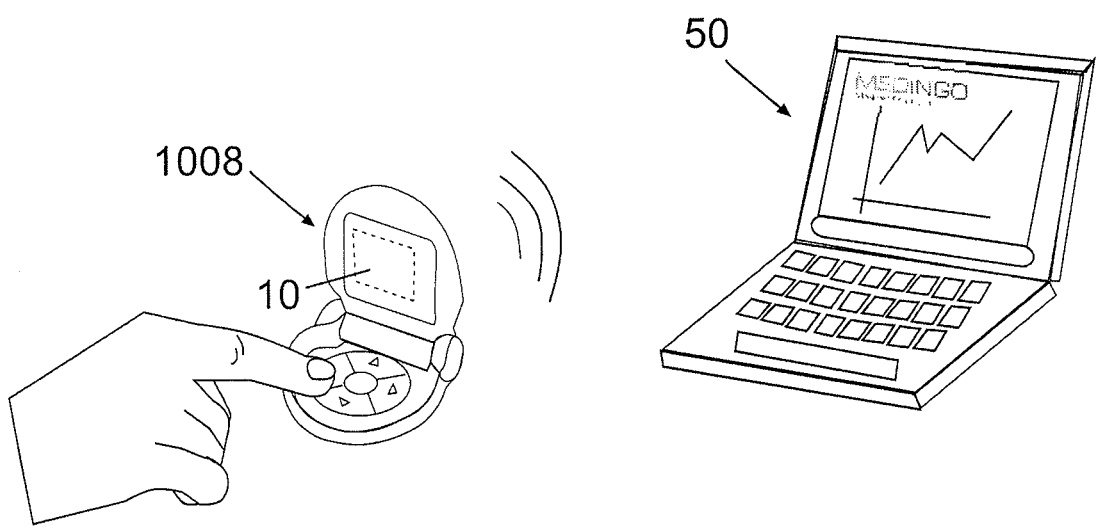
FIG. 11 illustrates exemplary CIR assessment feature located in a remote control unit and in a PC.

FIG. 11 illustrates another exemplary embodiment of the insulin delivery system where the CIR assessment feature (10) is configured to be located in a remote control unit (1008) that communicates with an external PC (50). According to this embodiment, any changes of the parameters representing the diabetic state of the user (e.g., CIR) can be saved and can be displayed in any graphical or non-graphical manner. In some embodiments, the saved data may automatically be sent to the patient's doctor or any other medical practitioner (e.g., by electronic mail or any other means) for evaluation, validation or any other clinical intervention.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made without departing from the spirit and scope of the invention. Other aspects, advantages, and modifications are considered to be within the scope of the disclosure. The claims presented are representative of at least some of the embodiments disclosed herein. Other presently unclaimed embodiments and/or inventions are also contemplated. The inventors reserve the right to pursue such embodiments/inventions in later claims.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

Any and all patents, applications, articles and/or publications referenced in this specification are hereby incorporated by reference herein in their entireties.

Although illustrative embodiments of the invention have been described in detail herein with reference to the accompanying drawings, it is to be understood that the invention is not limited to those embodiments, and that various changes and modifications can be effected therein by one skilled in the art without departing from the scope and spirit of the invention.

What is claimed is:

1. A computer-implemented method of determining an assessed carbohydrate to insulin ratio ($CIR_{new}$) of a patient, the method being performed by execution of computer program instructions by one or more processors, the method, comprising:
   receiving, by one or more processors, an initial set of values comprising at least a normoglycemia glucose level ($BG_0$). a target glucose level (TBG), an insulin sensitivity (IS), and, an estimated carbohydrate to insulin ratio ($CIR_{old}$);
   receiving, by one or more processors, a Carb value representing a planned meal of a content having a known carbohydrate load (Carb);
   receiving or determining, by one or more processors, a test bolus value based on the determined initial set of values and the Carb value;
   receiving or determining, by one or more processors, a post-prandial glucose level (CBG) of the patient subsequent to administration of the test bolus and consumption of the planned meal;
   determining, by one or more processors, the assessed carbohydrate to insulin ratio ($CIR_{new}$) of the patient based on the initial set of values and the post-prandial glucose level (CBG) of the patient;
   wherein the determination of the post-prandial glucose level (CBG) is repeated, by one or more processors, until either:
      a substantially constant glucose level ($BG_1$) is achieved, and/or
      a normal post-prandial glucose level is achieved.

2. The computer-implemented method of claim 1, wherein if a difference between the normoglycemia glucose level value and the post-prandial glucose level value is within a predefined range, then the assessed carbohydrate to insulin ratio is determined to be substantially the same as the initial carbohydrate to insulin ratio of the patient.

3. The computer-implemented method of claim 1, wherein if a difference between the normoglycemia glucose level value and the post-prandial glucose level value does not fall within a predefined range, then the carbohydrate to insulin ratio is reassessed.

4. The computer-implemented method of claim 1, wherein if a difference in glucose values calculated by subtracting the normoglycemia blood glucose level value from the post-prandial glucose level value is less than a predefined absolute value, then the carbohydrate to insulin ratio is reassessed.

5. The computer-implemented method of claim 1, wherein the known meal content comprises carbohydrates with a relatively high glycemic index.

6. The computer-implemented method of claim 1 further comprising, if a difference in the glucose values calculated by subtracting the normoglycemia glucose level value from the post-prandial glucose level value is greater than a predefined value, advising the patient to administer a correction bolus.

7. The computer-implemented method of claim 1 further comprising, if a difference in the glucose values calculated by subtracting the post-prandial glucose level value from the normoglycemia glucose level value is greater than a predefined value, advising the patient to consume an amount of carbohydrates to achieve the target glucose level.

8. The computer-implemented method of claim 1, wherein prior to determining the initial set of values, the patient is required to fast for a period of time.

9. The computer-implemented method of claim 8, wherein the period of time is at least three hours.

10. The computer-implemented method of claim 1, wherein prior to determining the initial set of values, the patient is required to achieve normoglycemia.

11. The computer-implemented method of claim 1, wherein after the receiving a confirmation that the test bolus dosage has been administered to the patient and prior to the determining the assessed carbohydrate to insulin ratio, the patient is required to achieve normoglycemia.

12. The computer-implemented method of claim 11, wherein the determination of normoglycemia is made by comparing the post-prandial glucose level of the patient to the target glucose level.

13. The computer-implemented method of claim 11, wherein while the normoglycemia is not achieved, the patient is repetitively required to perform a glucose correction.

14. The computer-implemented method of claim 13, wherein the post-prandial glucose level of the patient is retested after each glucose correction.

15. The computer-implemented method of claim 13, wherein the glucose correction comprises at least one of the administering a correction bolus and consuming a correction glucose.

16. The computer-implemented method of claim 15, wherein the assessed carbohydrate to insulin ratio is determined based on the correction bolus.

17. The computer-implemented method of claim 15, wherein the assessed carbohydrate to insulin ratio is determined based on the correction glucose.

18. The computer-implemented method of claim 13, wherein the patient is repetitively required to perform the glucose correction during a predetermined period of time.

19. A system for determining an assessed carbohydrate to insulin ratio ($CIR_{new}$) of a patient, comprising:
- a memory component adapted for storing an initial set of values comprising at least a normoglycemia glucose level ($BG_0$), a target glucose level (TBG), an insulin sensitivity(IS), and, an estimated carbohydrate to insulin ratio ($CIR_{old}$);
- a user interface component adapted for selecting a meal of a content having a known carbohydrate load (Carb);
- a bolus selection component adapted for selecting a test bolus dosage based on the stored initial set of values and the planned meal;
- a glucose sensing component adapted for periodically determining a post-prandial glucose level (CBG) of the patient subsequent to administration of the test bolus dosage and consumption of the planned meal; and,
- a CIR assessment component comprising one or more processors executing computer program instructions adapted for determining the assessed carbohydrate to insulin ratio ($CIR_{new}$) of the patient based on the initial set of values and the post-prandial glucose level value (CBG);
- wherein the determination of the post-prandial glucose level (CBG) is repeated until either:
  - a substantially constant glucose level ($BG_1$) is achieved, and/or
  - a normal post-prandial glucose level is achieved.

20. The system of claim 19, wherein if a difference between the normoglycemia glucose level value and the post-prandial glucose level value is within a predefined range, then the assessed carbohydrate to insulin ratio is determined by one or more processors to be substantially the same as the initial carbohydrate to insulin ratio of the patient.

21. The system of claim 19, wherein if a difference between the normoglycemia glucose level value and the post-prandial glucose level value does not fall within a predefined range, then the carbohydrate to insulin ratio is reassessed.

22. The system of claim 19, wherein if a difference between the normoglycemia glucose level value and the post-prandial glucose level value is less than a predefined absolute value, then the assessed carbohydrate to insulin ratio is determined by one or more processors to be substantially the same as the initial carbohydrate to insulin ratio of the patient.

23. The system of claim 19, wherein the known meal content comprises carbohydrates with a relatively high glycemic index.

24. The system of claim 19 wherein, if a difference in the glucose values calculated, by one or more processors, by subtracting the normoglycemia glucose level value from the post-prandial glucose level value is greater than a predefined value, the user interface component is further adapted for advising the patient to administer a correction bolus.

25. The system of claim 19 wherein, if a difference in the glucose values calculated, by one or more processors, by subtracting the post-prandial glucose level value from the normoglycemia glucose level value is greater than a predefined value, the user interface component is further adapted for advising the patient to consume an amount of carbohydrates to achieve the target glucose level.

26. The system of claim 19, wherein the user interface component is adapted for advising the patient to fast for a period of time prior to determining the initial set of values.

27. The system of claim 26, wherein the period of time is at least three hours.

28. The system of claim 19, wherein the user interface component is further adapted for advising the patient to achieve normoglycemia prior to determining the initial set of values.

29. The system of claim 19, wherein the user interface component is further adapted for advising the patient to achieve normoglycemia after a confirmation that the test bolus dosage has been administered is received.

30. The system of claim 29, wherein the determination of normoglycemia is made by comparing the post-prandial glucose level of the patient to the target glucose level.

31. The system of claim 29, wherein while the normoglycemia is not achieved, the user interface component is adapted for repetitively requiring the patient to perform a glucose correction.

32. The system of claim 31, wherein the glucose sensing component retests the post-prandial glucose level of the patient after each glucose correction.

33. The system of claim 32, wherein the glucose correction comprises at least one of the administering a correction bolus and consuming a correction glucose.

34. The system of claim 33, wherein the assessed carbohydrate to insulin ratio is determined by one or more processors based on the correction bolus.

35. The system of claim 34, wherein the assessed carbohydrate to insulin ratio is determined by one or more processors based on the correction glucose.

36. The system of claim 33, wherein the user interface is further adapted for requiring the patient to perform the glucose correction during a predetermined period of time.

37. The system of claim 19 further comprising an insulin infusion component coupled to said glucose sensing component.

38. The system according to claim 37, wherein said insulin infusion component is configured as a patch unit adherable to the skin of the patient.

39. The system according to claim 38, further comprising a remote control unit configured to communicate with the patch unit and further configured to allow programming and data acquisition.

40. The system according to claim 39, wherein said CIR assessment component resides in the remote control unit.

41. The system of claim 19, wherein the glucose sensing component is a glucose monitor.

42. The system of claim 41, wherein the glucose monitor is a glucometer.

43. The system of claim 41, wherein the glucose monitor is a CGM.

44. The method of claim 1, wherein if the substantially constant glucose level ($BG_1$) is achieved, the assessed carbohydrate to insulin ration ($CIR_{new}$) is calculated by one or more processors as:

$$CIR_{new} = \frac{CIR_{old} * Carb}{Carb + CIR_{old} * \frac{CBG - TBG}{IS}}$$

when the difference ($\Delta BG$) between $BG_1$ and $BG_0$ is larger than a predefined value (Y) and $$CIR_{new} = \frac{Carb}{\frac{Carb}{CIR_{old}} - \frac{\Delta BG}{IS}}$$

when the difference ($\Delta BG$) between $BG_1$ and $BG_0$ is larger than a predefined value (Y);
or if the normal post-prandial glucose level is achieved, the assessed carbohydrate to insulin ratio ($CIR_{new}$) is calculated as:

$$CIR_{new} = CIR_{old} \cdot \frac{\sum_{i=1}^{n}(Carb + CG_i)}{\sum_{i=1}^{n}(Carb + CB_i \cdot CIR_{old})}$$

where:
n=number of periods used for determining the assessed carbohydrate to insulin ratio ($CIR_{new}$),
i=a counter designating each period,
$CB_i$=a correction bolus needed when CBG is above TBG, and
$CG_i$=a glucose correction needed when CBG is below TBG.

45. The system of claim 19, wherein if the substantially constant glucose level ($BG_1$) is achieved, the assessed carbohydrate to insulin ration ($CIR_{new}$) is calculated by one or more processors as:

$$CIR_{new} = \frac{CIR_{old} * Carb}{Carb + CIR_{old} * \frac{CBG - TBG}{IS}}$$

when the difference ($\Delta BG$) between $BG_1$ and $BG_0$ is larger than a predefined value (Y) and $$CIR_{new} = \frac{Carb}{\frac{Carb}{CIR_{old}} - \frac{\Delta BG}{IS}}$$

when the difference ($\Delta BG$) between $BG_1$ and $BG_0$ is larger than a predefined value (Y);
or if the normal post-prandial glucose level is achieved, the assessed carbohydrate to insulin ratio ($CIR_{new}$) is calculated as:

$$CIR_{new} = CIR_{old} \cdot \frac{\sum_{i=1}^{n}(Carb + CG_i)}{\sum_{i=1}^{n}(Carb + CB_i \cdot CIR_{old})}$$

where:
n=number of periods used for determining the assessed carbohydrate to insulin ratio ($CIR_{new}$),
i=a counter designating each period,
$CB_i$=a correction bolus needed when CBG is above TBG, and
$CG_i$=glucose correction needed when CBG is below TBG.

46. The system of claim 45, wherein the correction bolus ($CB_i$) needed when the post-prandial glucose level (CBG) is above the target glucose level (TBG) is calculated by one or more processors as follows:

$$CB_i = \frac{CBG - TBG}{IS}.$$

\* \* \* \* \*